(12) United States Patent
Miteva et al.

(10) Patent No.: US 11,020,378 B2
(45) Date of Patent: Jun. 1, 2021

(54) COMPOUNDS, COMPOSITIONS AND METHODS FOR TREATING INSULIN RESISTANCE

(71) Applicants: UNIVERSITE PARIS DESCARTES, Paris (FR); UNIVERSITÉ PARIS-SUD 11, Orsay (FR); INSTITUT NATIONAL DE LA SANTE ET DE LA RECHERCHE MEDICALE, Paris (FR); UNIVERSITE PARIS DIDEROT, Paris (FR); CENTRE NATIONAL DE LA RECHERCHE SCIENTIFIQUE, Paris (FR)

(72) Inventors: Maria Miteva, Antony (FR); Bruno Villoutreix, Vincennes (FR); David J. Aitken, Orsay (FR); Anne-Françoise Burnol, Sèvres (FR); Anais Gondoin, Antony (FR); Tarik Issad, Paris (FR)

( * ) Notice: Subject to any disclaimer, the term of this patent is extended or adjusted under 35 U.S.C. 154(b) by 0 days.

(21) Appl. No.: 16/496,111

(22) PCT Filed: Mar. 20, 2018

(86) PCT No.: PCT/EP2018/056931
§ 371 (c)(1),
(2) Date: Sep. 20, 2019

(87) PCT Pub. No.: WO2018/172306
PCT Pub. Date: Sep. 27, 2018

(65) Prior Publication Data
US 2020/0030297 A1  Jan. 30, 2020

(30) Foreign Application Priority Data
Mar. 20, 2017  (FR) ...................... 1752287

(51) Int. Cl.
| A61K 31/422 | (2006.01) |
| A61P 3/10 | (2006.01) |
| A61K 31/341 | (2006.01) |
| A61K 31/42 | (2006.01) |
| A61K 31/513 | (2006.01) |

(52) U.S. Cl.
CPC .......... *A61K 31/422* (2013.01); *A61K 31/341* (2013.01); *A61K 31/42* (2013.01); *A61K 31/513* (2013.01); *A61P 3/10* (2018.01)

(58) Field of Classification Search
CPC .................................................. A61K 31/422
See application file for complete search history.

(56) References Cited

U.S. PATENT DOCUMENTS 3,427,318 A    2/1969  Barber et al.
2014/0023603 A1*  1/2014  Chung ...................... A61P 9/00
                                                                 424/62
2020/0316070 A1*  10/2020  Meffre .................. A61K 31/515

FOREIGN PATENT DOCUMENTS

WO    2000055634    9/2000

OTHER PUBLICATIONS

Holt et al. Biochem J. 2005, 388, 393-406 (Year: 2005).*
Emili et al. Ann. Intern. Med. 2005, 142, 611-619 (Year: 2005).*
Kodera et al. Biochemical and Biophysical Research Communications 2014, 443, 828-833 (Year: 2014).*
International Search Report issued in corresponding International patent application No. PCT/EP2018/056931 dated Jul. 30, 2018, 7 pages.
Witten Opinion issued in corresponding International patent application No. PCT/EP2018/056931 dated Jul. 30, 2018, 8 pages.
Marwaha, et al. "N-Acylated Derivatives of Sulfamethoxazole and Sulfafurazole Inhibit Intracellular Growth of Chlamydia trachomatis." Antimicrobial Agents and Chemotherapy Journal, vol. 58, No. 5. pp. 2968-2971. May 2014.

(Continued)

*Primary Examiner* — Matthew P Coughlin
(74) *Attorney, Agent, or Firm* — Pearne & Gordon LLP

(57) ABSTRACT

The invention relates to a compound inhibiting the interaction between a Grb14 protein and an insulin receptor of Formula (I) or Formula (II),

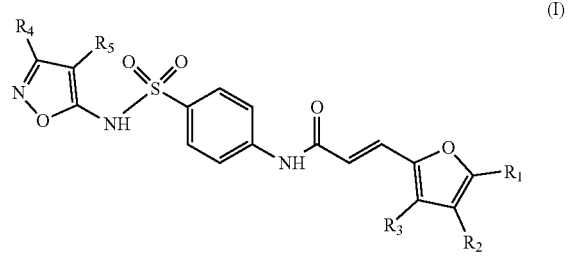

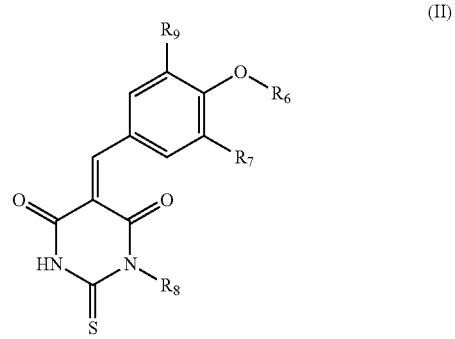

their salts, solvates, and/or diastereoisomers, for use for therapeutic purposes, in particular for the treatment of insulin resistance, and to pharmaceutical compositions containing such compounds.

19 Claims, 4 Drawing Sheets

(56) References Cited

OTHER PUBLICATIONS

Figure 1:
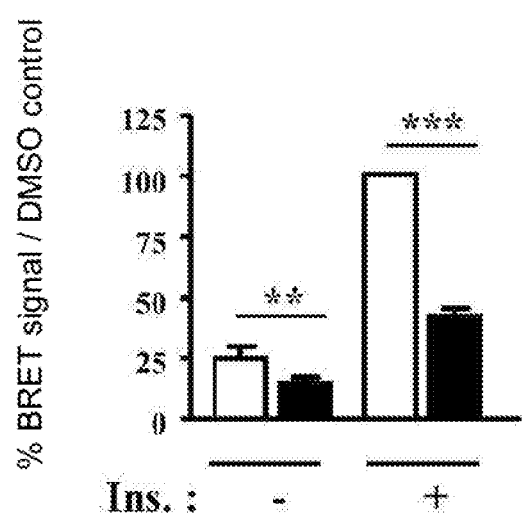

Desbuquois, et al. "Regulation of insulin and type 1 insulin-like growth factor signaling and action by the Grb10/14 and SH2B1/B2 adaptor proteins." FEBS Journal, vol. 280. pp. 794-816 (2013).

Holt, et al. "Grb10 and Grb14: enigmatic regulators of insulin action—and more?" Biochem Journal, vol. 388. pp. 393-406. Feb. 22, 2005.

Menke, et al. "Prevalence of and Trends in Diabetes Among Adults in the United States, 1988-2012." JAMA, vol. 314, No. 10. pp. 1021-1029. Sep. 8, 2015.

Executive Summary of the Third Report of the National Cholesterol Education Program (NCEP) Expert Panel on Detection, Evaluation and Treatment of High Blood Cholesterol in Adults (Adult Treatment Panel III). American Medical Association. JAMA, vol. 285, No. 19. pp. 2486-2497. May 16, 2001.

Pontiki, et al. "Design, synthesis and pharmacobiological evaluation of novel acrylic acid derivatives acting as lipoxygenase and cyclooxygenase-1 inhibitors with antioxidant and anti-inflammatory activities." European Journal of Medicinal Chemistry, vol. 46, pp. 191-200. 2011.

Zimmet, et al. "Nouvelle définition globale du syndrome métabolique: raisonnement et résultats." Diabetes Voice. vol. 50, No. 3. pp. 31-33. Sep. 2005.

English Translation of Written Opinion in PCT/EP2018/056931 dated Jul. 30, 2018, 10 pages.

Gondoin, et al. "Controle de la signalisation et de l'action de l'insuline par la proteine Grb14." Biologie Aujourd'hui. vol. 208, pp. 119-136. 2014.

World Health Organization. "Definition, Diagnosis, and Classification of Diabetes Mellitus and its Complications." 1999.

Uciechowska, et al. "Thiobarbiturates as Sirtuin Inhibitors: Virtual Screening, Free-Energy Calculations, and Biological Testing." ChemMedChem, vol. 3. pp. 1965-1976. 2008.

Park, Jung Sup. "Studies on the Synthesis and Antimicrobial Activity of 2-Aryl-3-(5-nitro-2-furyl) acrylamides." Journal of the Pharmaceutical Society of Korea. vol. 18, pp. 249-254. 1974.

Burnol, et al. "Grb-14—Physio 2006."

\* cited by examiner

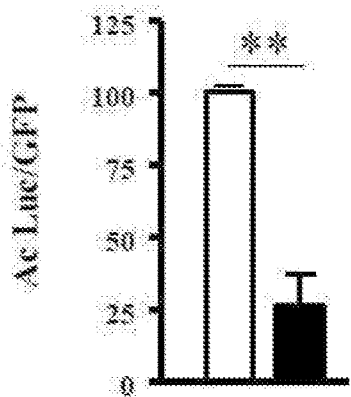 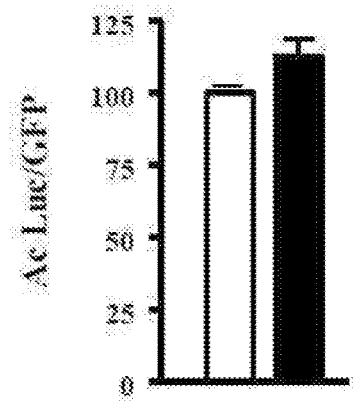
FIG. 3A  FIG3B
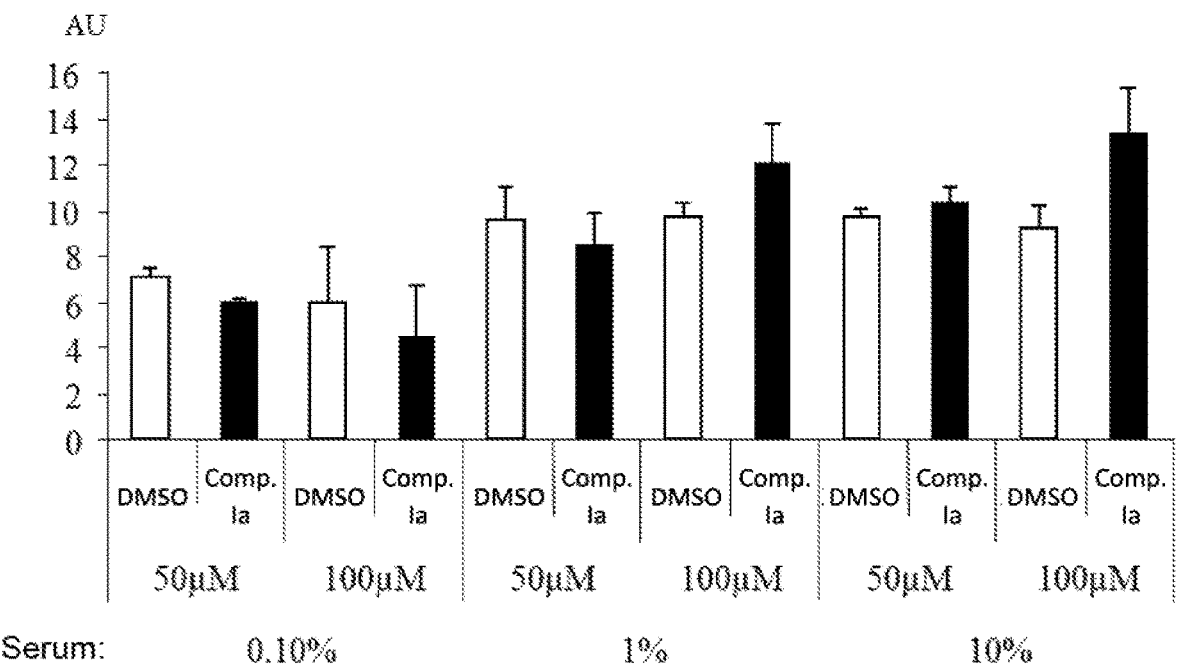
FIG. 4

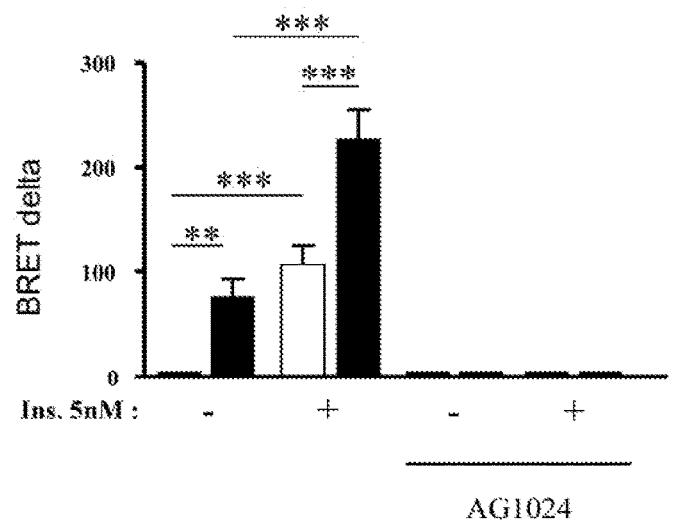
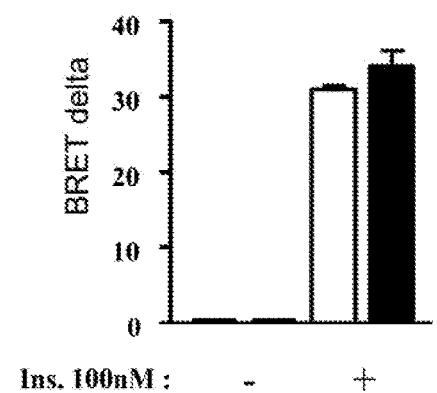
FIG. 5A  FIG5B
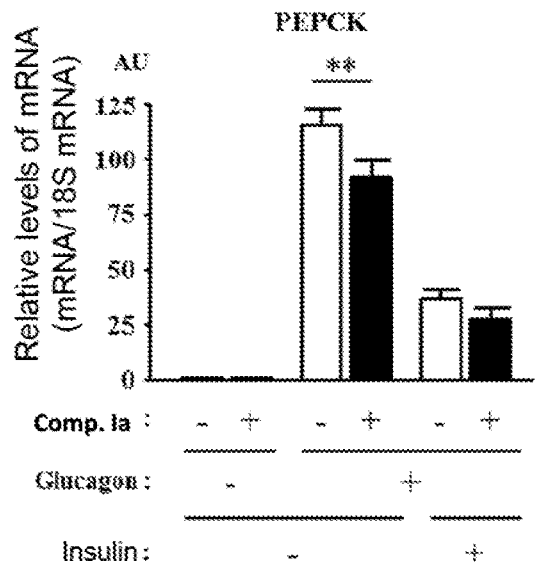
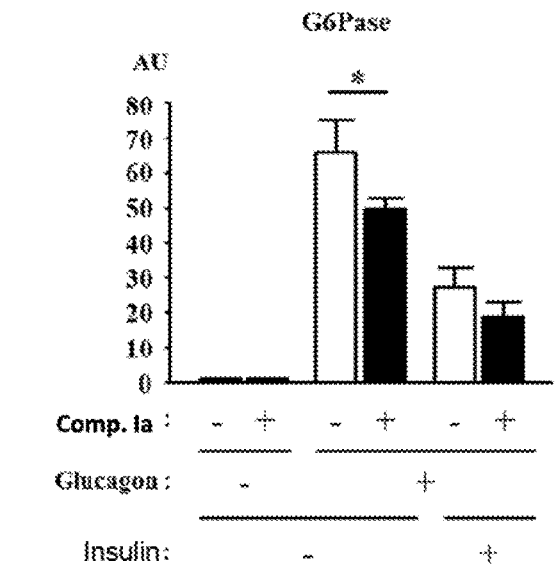
FIG. 6

COMPOUNDS, COMPOSITIONS AND METHODS FOR TREATING INSULIN RESISTANCE

The present invention relates to inhibitors of the interaction between the Grb14 protein and the insulin receptor for use for therapeutic purposes, in particular for the treatment of insulin resistance, as well as for the prevention and treatment of pathologies associated with insulin resistance. The invention also relates to a method for the synthesis of these inhibitors and pharmaceutical compositions comprising said inhibitors.

PRIOR ART

For many years, there has been a sharp increase in metabolic diseases such as diabetes, especially type 2 diabetes, obesity, metabolic syndrome and pre-gestational diabetes. For example, the World Health Organization estimates that in 2016 there were more than 400 million people with diabetes worldwide and indicates that the global prevalence of diabetes among adults over 18 has increased from 4.7% in 1980 to 8.5% in 2014.

Type 2 diabetes accounts for 90% of all diabetes worldwide. It is largely the result of being overweight and sedentary. The annual health care cost in the United States for diabetes was estimated at $245 billion in 2012. Preventing and treating metabolic diseases such as type 2 diabetes have become a major health care priority. In addition, abnormal glucose homeostasis is directly and indirectly associated with hypertension and alterations in lipid metabolism, and patients with type 2 diabetes have a significantly increased risk of macrovascular and microvascular complications, such as high blood pressure, diabetic microangiopathy, or diabetic macroangiopathy.

Current therapeutic strategies used to control the majority of these metabolic diseases and their consequences aim to improve insulin secretion or its actions in the different target tissues. Metformin is generally recommended as a first-line treatment. Other drugs include: other biguanides, sulfonylureas, thiazolidinediones, dipeptidyl peptidase-4 inhibitors, alpha-glucosidase inhibitors, glinides, fibrates, SGLT2 inhibitors, and glucagon-like peptide-1 (GLP1) analogues. Most subjects do not initially require insulin, but insulin therapy may optionally be associated with oral medication.

Nevertheless, the majority of these metabolic diseases are associated with insulin resistance and the latter is initiated well in advance of the diabetic state. Thus, in a recent study, it is estimated that in the United States, more than 37% of adults have pre-diabetic conditions (Menke A et al., 2015), most of which involving the development of insulin resistance. Insulin resistance leads to impaired insulin signaling and reduced effectiveness of conventional therapeutic approaches. For pre-diabetic conditions, resistance to insulin develops before the onset of hyperglycemia and is associated with an increase in insulin production. After several years, the increase in insulin secretion is no longer sufficient to compensate for the resistance to insulin of insulin-dependent tissues and the subject becomes hyperglycemic. The beta cells of the pancreas can no longer produce enough insulin to compensate for the decrease in insulin sensitivity, they begin to lose their function and apoptosis is triggered. Thus, in parallel with the development of insulin resistance, there is a progressive loss of the functional mass of pancreatic cells. Eventually, this loss of functional cell mass is such that the pancreas is no longer able to compensate for the loss of insulin sensitivity, leading to the development of type 2 diabetes. However, none of the drugs usually used to treat diabetes are known to permanently block the natural progression of the disease. Thus, more than half of the "pre-diabetic" population will develop type 2 diabetes after 4 to 5 years of treatment. For example, metformin would only reduce the risk of diabetes by 4%.

In addition, all current oral antidiabetics have significant side effects that significantly reduce their benefit/risk ratio during chronic preventive treatment in asymptomatic subjects. For example, increased risks of heart failure or bladder cancer associated with treatments containing insulin sensitizers, such as rosiglitazone or pioglitazone (belonging to the thiazolidinedione family) have led to their withdrawal from the market by various health authorities.

Grb14 is a molecular adapter strongly expressed in insulin-sensitive tissues (liver, adipose tissue, muscle), which binds to the activated insulin receptor and inhibits its catalytic activity. Grb14 expression is increased in adipose tissue of patients with type 2 diabetes, as well as in different animal models of insulin resistance, suggesting that this protein may be involved in decreasing insulin signaling. The peptide domains of the proteins of the Grb7 family involved in inhibiting the tyrosine kinase activity of insulin receptors have been identified in WO200055634, however this patent application does not provide molecules that can effectively treat insulin resistance. Thus, there is a need for new compounds capable of addressing the problems caused by existing treatments, allowing insulin resistance to be treated and thus for preventing or treating pathologies associated with insulin resistance.

Technical Problem

The invention therefore aims to overcome the disadvantages of the prior art. In particular, the invention aims to provide new inhibitors of the interaction between Grb14 and the insulin receptor for use for therapeutic purposes. Where these molecules can be used especially in pharmaceutical compositions for therapeutic purposes.

More particularly, the present invention provides new compositions based on these inhibitors for use in the treatment of insulin resistance. Typically, the compositions and methods provided by the inventors can be used to treat a subject suffering from insulin resistance. Thus, the compositions and methods provided by the inventors can be used to treat a subject suffering, at risk of suffering or likely to suffer from a pathology associated with insulin resistance.

Another objective of the present invention is to provide a method for preparing these compounds.

BRIEF DESCRIPTION OF THE INVENTION

To this end, the invention relates to a compound inhibiting the interaction between a Grb14 protein and an insulin receptor selected from the group consisting of compounds belonging to the family of sulfonamide isoxazoles of Formula (I), their salts, solvates, and/or diastereoisomers,

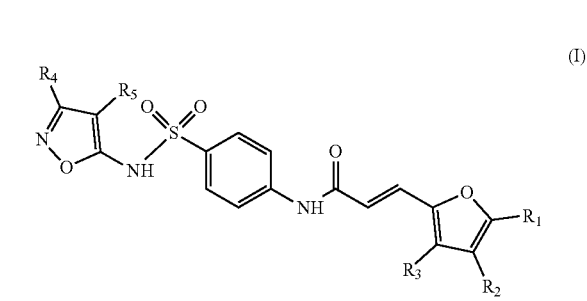

wherein:
the group $R_1$ represents a linear, cyclic or branched-chain alkyl group containing up to 5 carbon atoms, and
the groups $R_2$, $R_3$, $R_4$, and $R_5$ are identical or different and represent a hydrogen atom or a linear, cyclic or branched-chain alkyl group containing up to 5 carbon atoms;

or in the group consisting of compounds belonging to the family of dioxo-thioxotetrahydro-pyrimidinylidene of Formula (II), their salts, solvates, and/or diastereoisomers,

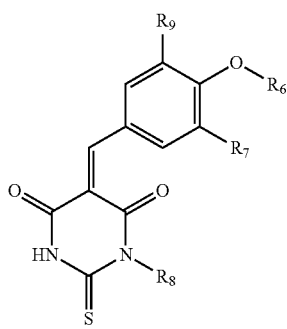

(II)

wherein:
the group $R_6$ represents a linear, cyclic or branched-chain alkyl group containing up to 5 carbon atoms or a —($C_1$-$C_5$ alkyl)-aryl group, with said aryl being substituted by one or more groups selected from the following groups: —$CO_2R_{11}$, $COR_{12}$, —$OC(O)R_{13}$, —$S(O)R_{14}$, —$OR_{15}$, —$SR_{16}$, —$SO_2R_{17}$, —$CONR_{18}R_{19}$, —$OCO_2R_{20}$,
the group $R_7$ represents a hydrogen atom or a carboxyl group,
the group $R_8$ represents a hydrogen atom or an aryl group, and
the group $R_9$ represents a hydrogen atom or an alkoxyl group,
the groups $R_{11}$ to $R_{20}$ are identical or different and represent a hydrogen atom or a linear, cyclic or branched-chain alkyl group containing up to 5 carbon atoms,
for its use for therapeutic purposes.

Unlike protein-protein interaction inhibitors, such as monoclonal antibodies or peptides, the compound inhibiting the interaction between a Grb14 protein and an insulin receptor according to the invention is a small molecule. By small molecule, within the meaning the invention, is meant a natural or synthetic compound having a molecular weight of less than 1200 Da, for example between 200 and 1100 Da, and preferably between 300 and 900 Da. As will be detailed below, the compounds of General Formula (I) and (II) are non-toxic, penetrate the membranes and stimulate in particular the PI3K pathway. In addition, there is a specificity of inhibition of the Grb14/IR interaction compared to the Grb10/IR interaction.

Advantageously, the compositions of the invention are used to increase lipogenesis and reduce neoglucogenesis and in particular to increase the action of insulin on the expression of genes involved in lipogenesis and neoglucogenesis.

Advantageously, inhibitors according to the invention are non-toxic compounds that penetrate membranes and stimulate in particular the PI3K pathway. In addition, these molecules specifically block the interaction between Grb14 and insulin receptors and do not interfere with the interaction between Grb10 and insulin receptors. These compounds are useful for therapeutic interventions for the treatment of insulin resistance and the prevention or treatment of pathologies associated with insulin resistance.

According to other optional features of the inhibitor compound:
the inhibitor compound of Formula (I) is such that:
the group $R_1$ represents a linear or branched-chain alkyl group containing up to 5 carbon atoms,
the groups $R_2$ and $R_3$ represent a hydrogen atom, and
the groups $R_4$ and $R_5$ represent a methyl group.

the inhibitor compound of Formula (I) is selected from the group consisting of compounds of Formula (Ia) or (Ib),

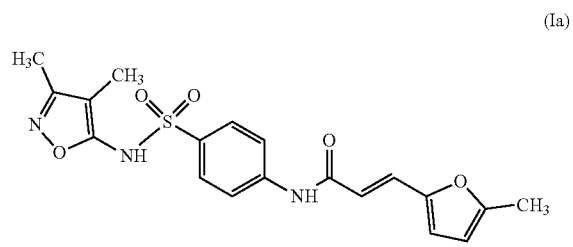

(Ia)

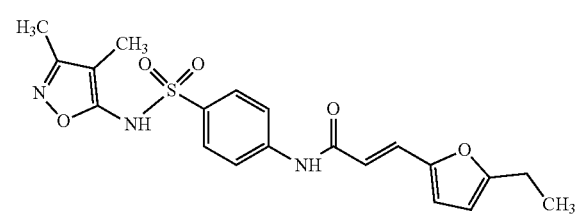

(Ib)

their salts, solvates, and/or diastereoisomers.

the inhibitor compound of Formula (II) is selected from the group consisting of compounds of Formula (IIc), (IId), (IIe), or (IIf)

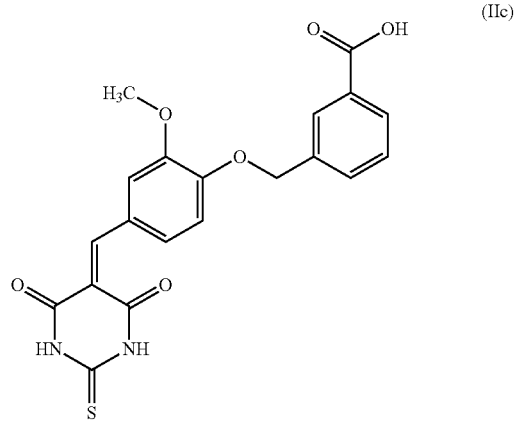

(IIc)

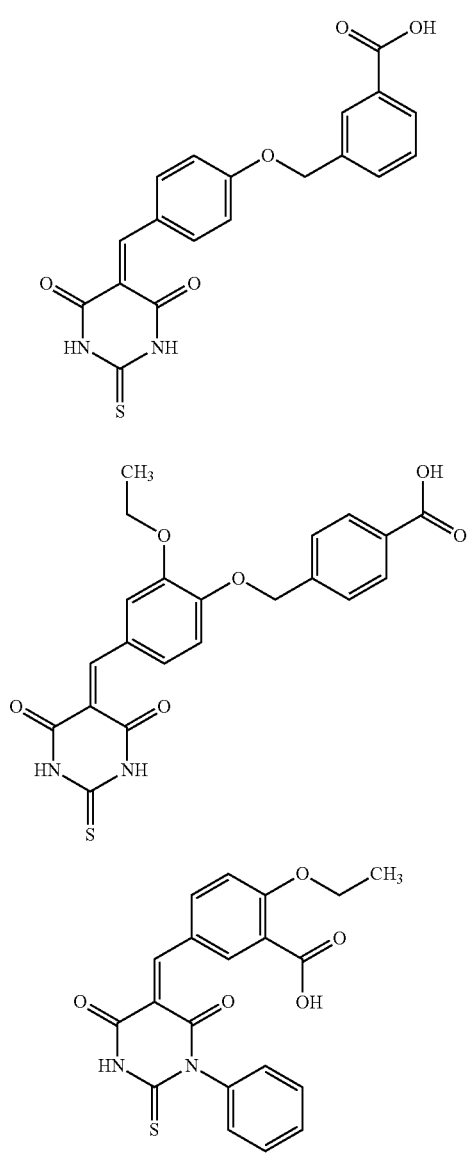

their salts, solvates, and/or diastereoisomers.

the inhibitor compound according to the invention is intended for use as an insulin sensitizer.

The invention also relates to a pharmaceutical composition comprising at least one inhibitor compound of Formula (I) or Formula (II) according to the invention.

According to other optional features of the composition:

the pharmaceutical composition according to the invention further comprises at least one other active ingredient selected from: sulfonylureas, biguanides, such as metformin, thiazolidinediones, GLP1 analogues, such as exenatide or liraglutide, dipeptidyl peptidase-4 inhibitors, such as gliptin, sitagliptin, vildagliptin, saxagliptin, linagliptin, gemigliptin, or alogliptin, alpha-glucosidase inhibitors, glinides, fibrates, or SGLT2 inhibitors, such as canaglifozine.

the pharmaceutical composition according to the invention is intended for use for therapeutic purposes in a subject subjected to insulin therapy, with said insulin therapy comprising insulin or an insulin analogue.

the pharmaceutical composition according to the invention is a combination product for simultaneous, joint or separate, or sequential use for therapeutic purposes.

The invention also relates to the inhibitor compound according to the invention or to the pharmaceutical composition according to the invention for their use in the treatment of insulin resistance, as well as for the prevention or treatment of a pathology associated with insulin resistance.

According to other optional features of this use:

the pathology associated with insulin resistance is selected from: metabolic syndrome, polycystic ovary syndrome, obesity, pre-gestational diabetes, type 2 diabetes, hyperglycemia, lipodystrophy, diabetic nephropathy, or cardiovascular complications, such as high blood pressure, diabetic microangiopathy, or diabetic macroangiopathy.

the inhibitor compound according to the invention is administered at a dose between 50 mg and 250 mg per day, preferably between 100 mg and 200 mg per day.

The invention also relates to a method for synthesizing an inhibitor compound according to Formula (I), or its diastereoisomers, comprising a step of condensing a sulfonamide of Formula (V)

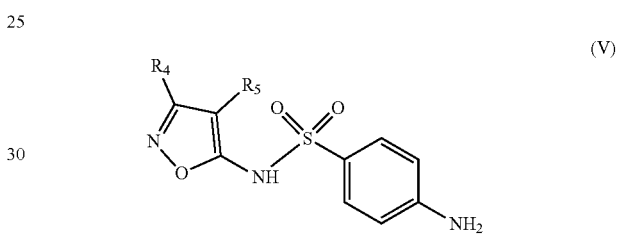

wherein:
the groups $R_4$ and $R_5$ are identical or different and represent a hydrogen atom or a linear, cyclic or branched-chain alkyl group containing up to 5 carbon atoms;
with an acrylic acid derivative of Formula (IV)

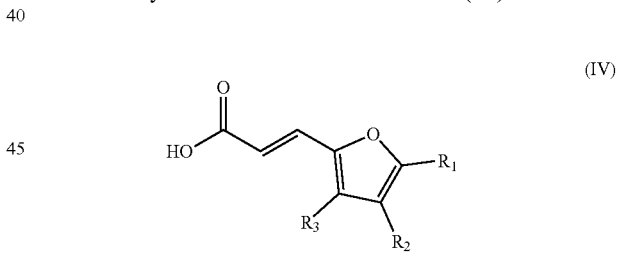

wherein:
the group $R_1$ represents a linear, cyclic or branched-chain alkyl group containing up to 5 carbon atoms, and
the groups $R_2$ and $R_3$ are identical or different and represent a hydrogen atom or a linear, cyclic or branched-chain alkyl group containing up to 5 carbon atoms.

In addition, according to an optional feature of this synthesis method, said condensation step is carried out in the presence of DIPEA (N-Ethyl-N-(propan-2-yl)propan-2-amine) and a peptide coupling reagent selected from HATU (1-[Bis(dimethylamino)methylene]-1H-1,2,3-triazolo[4,5-b]pyridinium 3-oxide hexafluorophosphate) and Ghosez's reagent (1-Chloro-N,N,2-trimethylpropenylamine).

Other advantages and features of the invention will appear upon reading the following description given by way of illustrative and non-limiting example, with reference to the appended Figures which represent:

FIG. 1, the inhibitory effect of the compound of Formula (Ia) (Comp. Ia) according to the invention (black bars) on the IR/Grb14 interaction measured by the IR-Luc/Grb14-YFP BRET technique in a cell-free system, compared to the control (white bars), in the presence or absence of a preliminary insulin (Ins.) stimulation at 100 nM. The results, expressed as a percentage of the DMSO (Dimethylsulfoxide) control, are the average calculated based on 2 to 8 independent experiments ($p<0.01$, *$p<0.001$, by Bonferroni Multiple comparison test).

Figure 2:
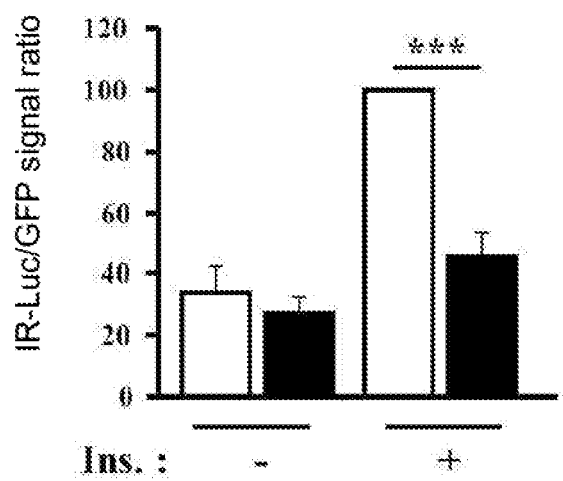

FIG. 2, the inhibitory effect of the compound of Formula (Ia) according to the invention (black bars) on the IR/Grb14 interaction as measured by co-immunoprecipitation in a cell-free system, compared to the control (white bars), with a western blot analysis of the amount of IR-Luc co-precipitated with Grb14-YFP, and a densitometric quantification of the revealed signals. The results, expressed as a percentage of the DMSO (Dimethylsulfoxide) control, are the average of 2 to 8 independent experiments (***$p<0.001$, by Bonferroni Multiple comparison test).

FIG. 3A and FIG. 3B, the inhibitory effect of the compound of Formula (Ia) according to the invention (black bars) on the interaction between Grb14 and the IR tyrosine kinase domain (IRTK-Grb14 interaction) as measured by co-immunoprecipitation with a western blot analysis of the amount of IRTK48-Rluc co-precipitated with Grb14 (FIG. 3A) or Grb10 (FIG. 3B) proteins fused to the YFP, and a densitometric quantification of the revealed signals. The results, expressed as a percentage of the DMSO (Dimethylsulfoxide) control, are the average of 3 independent experiments (**$p<0.01$, by t-test).

FIG. 4, the effect of the compound of Formula (Ia) (black bars) on the growth and survival of HEK293T cells measured after 72 h of culture compared to the DMSO (Dimethylsulfoxide) control (white bars). The histograms represent the cell growth rate determined by the ratio: Fluorescence at D3/Fluorescence at D0. The results are the average of 3 independent experiments carried out in triplicate.

FIG. 5A and FIG. 5B, the effect of the compound of Formula (Ia) according to the invention (black bars) on the activation of the PI3K/Akt pathway measured by the Luc-Akt-PH/YFP-membrane BRET technique compared to the DMSO (Dimethylsulfoxide) control (white bars) as measured on (FIG. 5A) HEK293T cells pre-incubated or not for 1 h with tyrosine kinase inhibitor AG1024 at a concentration of 25 µM final or on (FIG. 5B) an MCF7 line doubly and stably transfected with the vectors encoding Luc-Akt-PH and YFP-membrane. The results, expressed as BRET delta, are the average of 3 to 8 independent experiments ($p<0.01$, *$p<0.001$, by Newman-Keuls multiple comparison test).

FIG. 6, the effect of the compound of Formula (Ia) according to the invention (black bars) on the expression of insulin target genes, PEPCK (FIG. 6A) and G6Pase (FIG. 6B), involved in the neoglucogenesis pathway. Hepatocytes in primary culture are cultured for 8 h in the presence of compounds of Formula (Ia) (50 µM), insulin (1 nM) and glucagon (pre-incubation 1 h at 10 nM). The relative quantification of mRNAs is performed by RT-qPCR. The values are related to the quantification of the 18S gene in the same sample in order to normalize the results. The results are the average of 3 to 5 independent experiments (*$p<0.05$, **$p<0.01$, by Anova followed by a Newman-Keuls test).

Figure 7:
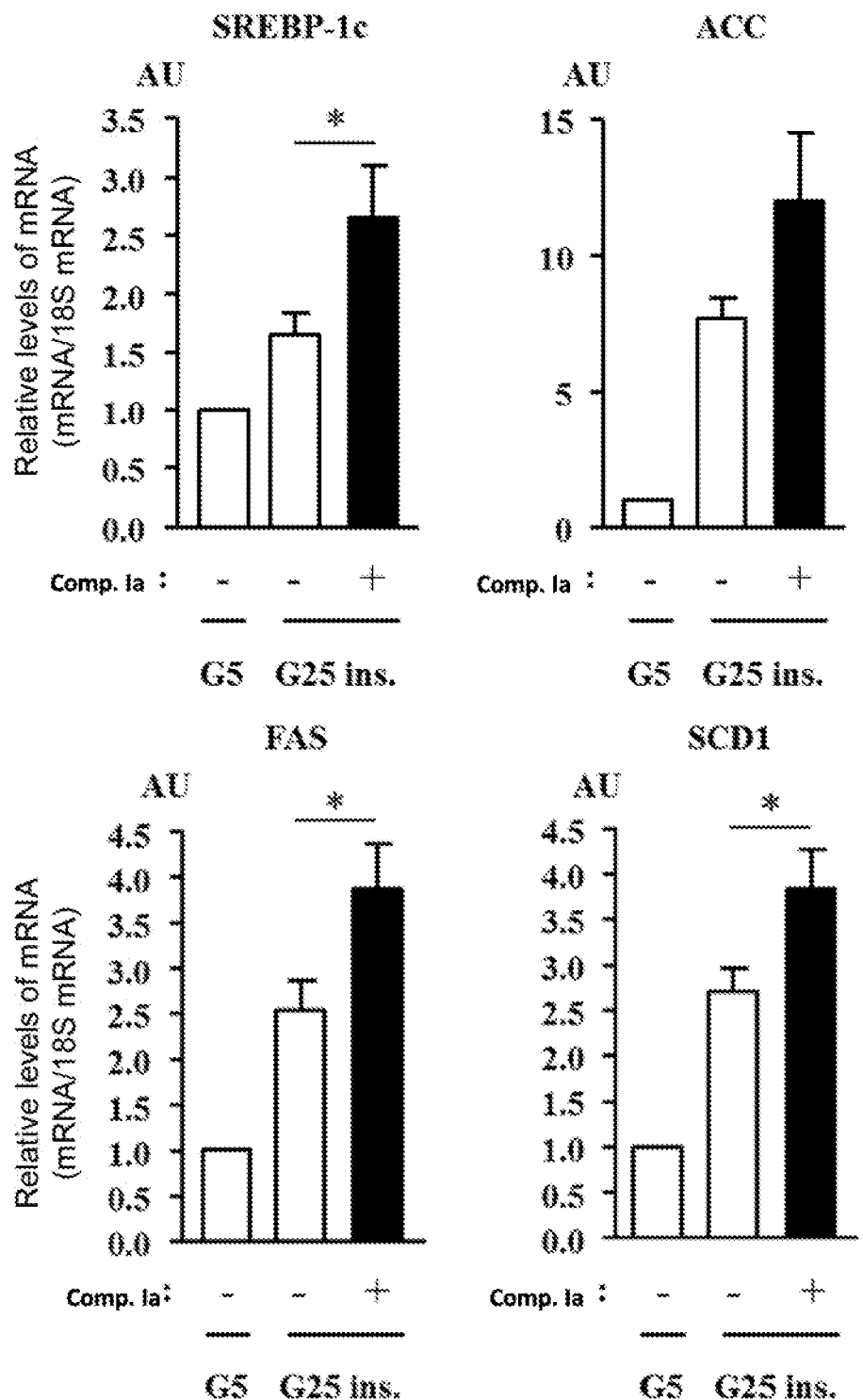

FIG. 7, the effect of the compound of Formula (Ia) according to the invention (black bars) on the expression of insulin target genes, SREBP-1c, ACC, FAS, and SCD1 (FIGS. 7A-D, respectively) involved in the lipogenesis pathway. Hepatocytes in primary culture are cultured in the presence of 5 mM glucose (G5) or 25 mM glucose (G25) and 10 nM insulin for 24 h. The relative quantification of mRNAs is performed by RT-qPCR. The values are related to the quantification of the 18S gene in the same sample in order to normalize the results. The results are the average of 3 to 5 independent experiments (*$p<0.05$ by Anova followed by a Newman-Keuls test).

DESCRIPTION OF THE INVENTION

The present invention provides a new therapeutic approach for the treatment of insulin resistance. The invention relates to new compounds, of the small molecule type, inhibiting the interaction between the Grb14 protein and the insulin receptor, as well as to pharmaceutical compositions containing such compounds for use for therapeutic purposes. The invention also relates to therapeutic methods using such compounds. The compounds, compositions and methods particularly allow for the treatment of insulin resistance, as well as for the prevention and treatment of pathologies associated with insulin resistance.

In the following description, the "Grb14 protein" corresponds, within the meaning of the invention, to a protein belonging to the Grb7 family of molecular adapters. The Grb7 family of molecular adapters consists of three members: Grb7, Grb10, and Grb14. All three bind to the activated, phosphorylated insulin receptor. However, only Grb10 and Grb14 appear to play an important role in regulating the action of insulin (Holt & Siddle 2005; Desbuquois et al. 2013). The Grb14 protein (NP_001290351; NP_004481. UniProtKB—Q14449), coded by the grb14 gene (Gene ID: 2888), has different isoforms defined by their species of origin: hGrb14 for humans, rGrb14 for rats, and mGrb14 for mice. Grb14 is known to be highly expressed in skeletal muscle, white adipose tissue, the heart, the brain, the pancreas, and the kidneys, as well as in the liver and the retina.

The "insulin receptor", within the meaning the invention, belongs to the family of receptors with tyrosine kinase (TK) activity. In humans, the insulin receptor is encoded by a single gene comprising 22 exons and 21 introns (Gene ID: 3643). The synthesis of the insulin receptor is subject to alternative splicing. Post-translational events downstream of either isoform result in the formation of a proteolytically cleaved α subunit and β subunit, which, when combined, are ultimately capable of a homo- or heterodimerization to produce the transmembrane insulin receptor ≈320 kDa (UniProtKB—P06213). The insulin receptor is located at the plasma membrane of most cells, but more strongly in insulin-sensitive tissues, such as the liver, muscle, and adipose tissue. It also is well expressed in the β cells of the pancreas, in the vascular endothelium, as well as in specific areas of the brain.

Within the meaning of the invention, "the inhibitor of the interaction between a Grb14 protein and an insulin receptor" corresponds to a compound capable of inhibiting the interaction between a Grb14 protein and an insulin receptor. In the context of the present invention, said inhibitor is preferably specific to the Grb14 protein and/or the insulin receptor, that is to say it does not inhibit the interaction of adapters of the same family with the insulin receptor, in particular Grb10.

Within the meaning of the invention, "insulin-sensitive tissues" refers to the liver, the pancreas, muscles, adipose tissues (white and brown), and the brain.

Within the meaning of the invention, the term "insulin resistance", also called "resistance to insulin", refers to the desensitization of cellular membrane receptors to insulin. As a result, insulin no longer has as much effect on these receptors. As a result, despite insulin, glucose no longer penetrates as much into the cells, and as a result, it accumulates in the blood and lymphatic circulation, resulting in an increase in blood sugar levels. This increase, in turn, stimulates hypersecretion of insulin by the pancreas and after a number of years, the pancreatic cells are exhausted. Classically, the clinical profile of people likely to develop or at risk of developing insulin resistance frequently comprises at least one, preferably several, more preferably at least three, of the following characteristics: overweight (BMI greater than 25), abnormal abdominal fat distribution (waist size greater than 80 cm in women, 94 cm in men), sedentary lifestyle, family history of type 2 diabetes, high blood pressure. Insulin resistance can be diagnosed by many methods known to the one skilled in the art, comprising glucose tolerance measurement, fasting insulin level measurement, insulin sensitivity measurement by intravenous glucose and insulin administration (hyperinsulinemic euglycemic clamp). The preferred method for measuring resistance to insulin is hyperinsulinemic euglycemic clamp.

By "pathology associated with insulin resistance" is meant, within the meaning of the invention, any pathology or condition that is the consequence of said insulin resistance or one of its comorbidities. Such pathologies are preferably selected from: metabolic syndrome, polycystic ovary syndrome, obesity, pre-gestational diabetes, type 2 diabetes, hyperglycemia, lipodystrophy, diabetic nephropathy, or cardiovascular complications, such as high blood pressure, diabetic microangiopathy (covering in particular diabetic neuropathy and diabetic retinopathy), and diabetic macroangiopathy.

By "metabolic syndrome" is meant, within the meaning of the invention, a pathology characterized by a plurality of asymptomatic physiological and biochemical anomalies that can coexist with genetic and acquired factors. Among the many definitions proposed, the diagnosis of the metabolic syndrome can be made using the following methods: the one from the World Health Organization (WHO) (WHO consultation 1999), the one from the National Cholesterol Education Program Adult Treatment Panel III (NCEP ATP III of 2001), and the one from the International Diabetes Federation (IDF 2005) (Zimmet et al., 2005). Preferably, the diagnosis is performed by the IDF 2005 method.

In the context of a preferred embodiment of the invention, the designation of a compound is intended to designate the compound itself, as well as any pharmaceutically acceptable salt, hydrate, or stereoisomer thereof. In a more preferred embodiment, the designation of a compound is intended to designate the compound as specifically designated in itself, as well as any pharmaceutically acceptable salt thereof.

For the purposes of the invention, by "pharmaceutically acceptable" is meant what is useful for the preparation of a pharmaceutical composition and what is generally safe and non-toxic for pharmaceutical use.

The expression "salt and/or solvate" is intended to refer, in the context of the present invention, to a salt or solvate of a compound according to the invention, preferably pharmaceutically acceptable and having the pharmacological activity of the corresponding compound. Thus, within the meaning of the invention, the term "salt" refers to a pharmaceutically acceptable, inorganic or organic, acid or base addition salt of a compound of the present invention. The formation of a salt typically consists of associating an acidic, basic, or zwitterionic molecule with a counterion to create a salt version of the compound. A wide variety of chemical species can be used in the neutralization reaction. Although most salts of a given active ingredient are bioequivalent, some may have, among other things, increased solubility or bioavailability properties. Salt selection is now a common operation in the drug development method as taught by H. Stahl and C. G. Wermuth (Stahl et al., 2011). Within the meaning of the invention, the term "solvates" corresponds to conventional solvates, such as those produced in the last stage of the preparation of the compounds of the invention due to the presence of solvents. For example, solvates due to the presence of water (these solvates are also called hydrates) or ethanol may be mentioned.

Within the meaning of the present invention, "stereoisomers" are compounds of the same semi-developed formula, but which differ in the arrangement of atoms in space. Within the meaning of the present invention, "enantiomers" are stereoisomers that are symmetrical to each other in a mirror and cannot be superimposed. Within the meaning of the present invention, "diastereoisomers" are stereoisomers that are not enantiomers. That is to say, diastereoisomers have the same sequence of atoms, but they can neither be superimposed nor are images of each other in a mirror. Traditionally, double bond stereochemistry is described either in cis or trans, with reference to the relative position of substituents on either side of a double bond.

By "subject" is meant here any member of the animal kingdom, preferably mammals, and more preferably human.

By the term "prevention" is to be understood, in the context of the present invention, preventing or delaying the onset of clinical or biochemical manifestations associated with the pathology. In the context of the prevention of insulin resistance-related diseases, the term "prevention" therefore refers to preventing or delaying the onset or decreasing the intensity of insulin resistance-related diseases, for example preventing or delaying the onset or decreasing the intensity of type 2 diabetes. Prevention can preferably be implemented in subjects considered at risk of developing or predisposed to develop the pathology.

In the context of the invention, the term "treatment" refers to treating a declared disease or pathology or alleviating its symptoms, and/or progression. Thus, the term "treatment" comprises a clinically or biochemically observed improvement in the subject's disease or pathology. Therefore, such treatment can be used in a subject with insulin resistance to delay its progression, reduce or suppress its effects, and thus treat this disease. Such treatment may also be used in a subject with a pathology associated with insulin resistance, such as metabolic syndrome, polycystic ovary syndrome, obesity, pre-gestational diabetes, type 2 diabetes, hyperglycemia, lipodystrophy, diabetic nephropathy, or cardiovascular complications, such as high blood pressure, diabetic microangiopathy, or diabetic macroangiopathy.

The term "administration" or "administer" means, in the context of the present invention, that a compound of interest is delivered or dispensed to a subject by any appropriate mode of administration, which may be easily determined by the one skilled in the art according to the nature of said compound. For example, said compound may be delivered or dispensed to said subject, as appropriate, by oral, transdermal, or parenteral route, such as by subcutaneous, intravenous, intramuscular, or intraperitoneal injection.

In the context of the present invention, by "pharmaceutically effective amount", is meant a prophylactic or therapeutic amount or concentration of a compound of interest, that is to say an amount or concentration of said compound sufficient to treat insulin resistance and/or to prevent or treat pathologies associated with insulin resistance, or to treat insulin resistance or said pathology once declared or to reduce its symptoms and/or progression. The one skilled in the art is able to determine this so-called pharmaceutically effective amount.

The expression "linear, cyclic or branched-chain alkyl group containing up to 5 carbon atoms", as used in the present invention (also called $C_1$-$C_5$ alkyl), corresponds to a saturated, linear, cyclic or branched hydrocarbon chain containing 1 to 5 carbon atoms, or an unsaturated, linear or branched hydrocarbon chain containing 2 to 5 carbon atoms. A saturated, linear, cyclic or branched hydrocarbon chain, containing 1 to 5 carbon atoms comprises, but is not limited to, methyl, ethyl, n-propyl, isopropyl, n-butyl, isobutyl, sec-butyl, t-butyl, n-pentyl, cyclopropyl, cyclobutyl, cyclopentyl, and the like. An unsaturated, linear or branched hydrocarbon chain, containing 2 to 5 carbon atoms, comprises at least one double or triple bond, and includes, but is not limited to, ethene, propene, butene, pentene, ethenyl, propenyl, butenyl, pentenyl, and the like.

The term "aryl group", as used in the present invention, refers to an aromatic hydrocarbon group preferably comprising 6 to 10 carbon atoms and comprising one or more, in particular 1 or 2, fused rings, such as a phenyl group or a naphthyl group. Advantageously, it refers to a phenyl group.

The term "—($C_1$-$C_5$ alkyl)-aryl", as used in the present invention, refers to an aryl group as defined above linked to the molecule via a C1-C5 alkyl group as defined above. In particular, the —($C_1$-$C_5$ alkyl)-aryl group according to the invention is a benzyl group. For groups comprising two or more subgroups, the attachment is indicated by "—". For example, "—($C_1$-$C_5$ alkyl)-aryl" refers to an alkyl radical linked to an aryl radical in which the alkyl is linked to the rest of the molecule.

The aryl group according to the present invention may be substituted with one or more groups independently selected from the group consisting of alkyl, alkoxyl (alkoxyl), hydroxyl, carboxyl, or ester. Examples of substituted phenyl groups are methoxyphenyl, dimethoxyphenyl, and carboxyphenyl.

The term "substituted", as used here, means that any one of the hydrogen atoms can be replaced by a substituent, such as a carboxyl group.

Inhibitor Compound According to the Invention

Unlike protein-protein interaction inhibitors, such as monoclonal antibodies or peptides, the compound inhibiting the interaction between a Grb14 protein and an insulin receptor according to the invention is a small molecule. By small molecule, within the meaning of the invention, is meant a natural or synthetic compound having a molecular weight between 200 and 1100 Da, preferably between 300 and 900 Da. These small molecules are generally more malleable by synthetic chemistry techniques than other classes of protein-protein interaction modulators, such as peptide compounds. In addition, they generally have a high structural complexity that gives them a high selectivity with respect to their target and a good binding affinity. Finally, they may have high bioavailability and the ability to cross membranes.

The object of the invention is a compound inhibiting the interaction between a Grb14 protein and an insulin receptor selected from the group consisting of compounds belonging to the family of sulfonamide isoxazoles of Formula (I), their salts, solvates, and/or diastereoisomers

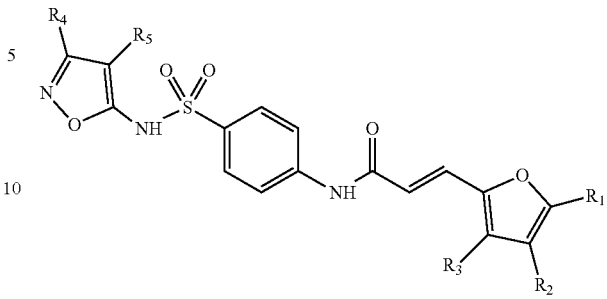

(I)

wherein:
the group $R_1$ represents a linear, cyclic or branched-chain alkyl group containing up to 5 carbon atoms, and
the groups $R_2$, $R_3$, $R_4$, and $R_5$ are identical or different and represent a hydrogen atom or a linear, cyclic or branched-chain alkyl group containing up to 5 carbon atoms;

or in the group consisting of compounds belonging to the family of dioxo-thioxotetrahydro-pyrimidinylidene of Formula (II), their salts, solvates, and/or diastereoisomers,

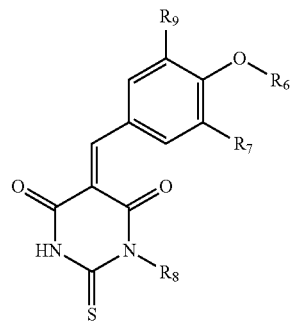

(II)

wherein:
the group $R_6$ represents a linear, cyclic or branched-chain alkyl group containing up to 5 carbon atoms or a —($C_1$-$C_5$ alkyl)-aryl group, with said aryl being substituted by one or more groups selected from the following groups: —$CO_2R_{11}$, $COR_{12}$, —$OC(O)R_{13}$, —$S(O)R_{14}$, —$OR_{15}$, —$SR_{16}$, —$SO_2R_{17}$, —$CONR_{18}R_{19}$, —$OCO_2R_{20}$,
the group $R_7$ represents a hydrogen atom or a carboxyl group,
the group $R_8$ represents a hydrogen atom or an aryl group,
the group $R_9$ represents a hydrogen atom or an alkoxyl group, and
the groups $R_{11}$ to $R_{20}$ are identical or different and represent a hydrogen atom or a linear, cyclic or branched-chain alkyl group containing up to 5 carbon atoms,
for its use for therapeutic purposes.

Family of Sulfonamide Isoxazoles

According to an embodiment of the first aspect of the present invention, the compound inhibiting the interaction between a Grb14 protein and an insulin receptor, for its use for therapeutic purposes, is selected from the group consisting of compounds belonging to the family of sulfonamide isoxazoles of Formula (I), their salts, solvates, and/or diastereomers

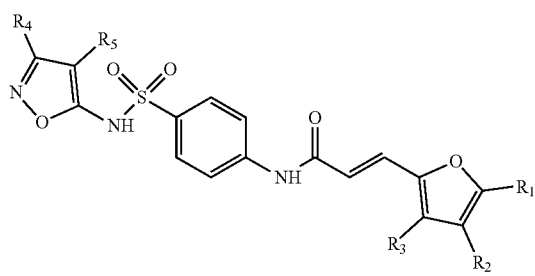

wherein:
- the group $R_1$ represents a linear, cyclic or branched-chain alkyl group containing up to 5 carbon atoms, and
- the groups $R_2$, $R_3$, $R_4$, and $R_5$ are identical or different and represent a hydrogen atom or a linear, cyclic or branched-chain alkyl group containing up to 5 carbon atoms.

Preferably, the compound of General Formula (I) is in trans configuration.

In particular, in this inhibitor compound of Formula (I), the groups $R_2$ and $R_3$ represent a hydrogen atom.

Also, in this inhibitor compound of Formula (I), the groups $R_4$ and $R_5$ represent a methyl group.

Preferably, in the inhibitor compound of Formula (I), the group $R_1$ represents a saturated, linear or branched-chain alkyl group containing up to 5 carbon atoms, preferably a saturated, linear or branched-chain alkyl group containing up to 3 carbon atoms.

More preferably, in the inhibitor compound of Formula (I), the group $R_1$ represents a saturated, linear chain alkyl group containing up to 5 carbon atoms, and even more preferably up to 3 carbon atoms.

Even more preferably, especially in the context of use according to the present invention, the inhibitor compound is selected from the group consisting of compounds of Formula (Ia) or Formula (Ib):

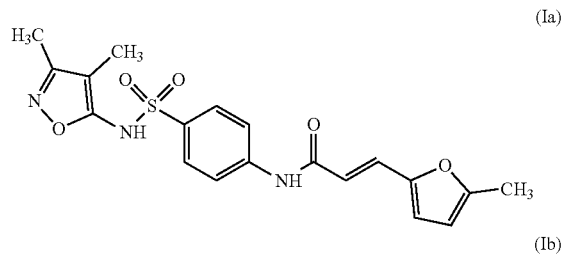

Inhibitor Compound of Formula (II)

According to an embodiment of the first aspect of the present invention, the compound inhibiting the interaction between a Grb14 protein and an insulin receptor, for its use for therapeutic purposes, is selected from the group consisting of compounds belonging to the family of dioxo-thioxo-tetrahydro-pyrimidinylidene of Formula (II), their salts, solvates, and/or diastereomers

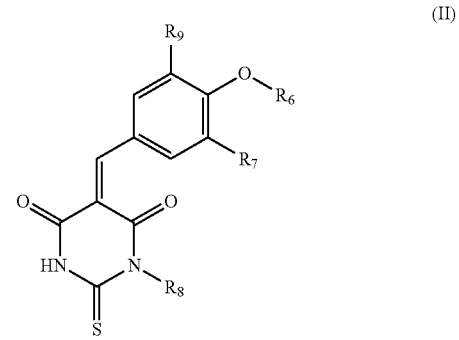

wherein:
- the group $R_6$ represents a linear, cyclic or branched-chain alkyl group containing up to 5 carbon atoms or a —($C_1$-$C_5$ alkyl)-aryl group, with said aryl being substituted by one or more groups selected from the following groups: —$CO_2R_{11}$, $COR_{12}$, —$OC(O)R_{13}$, —$S(O)R_{14}$, —$OR_{15}$, —$SR_{16}$, —$SO_2R_{17}$, —$CONR_{18}R_{19}$, —$OCO_2R_{20}$,
- the group $R_7$ represents a hydrogen atom or a carboxyl group,
- the group $R_8$ represents a hydrogen atom or an aryl group,
- the group $R_9$ represents a hydrogen atom or an alkoxyl group, and
- the groups $R_{11}$ to $R_{20}$ are identical or different and represent a hydrogen atom or a linear, cyclic or branched-chain alkyl group containing up to 5 carbon atoms.

Preferably, the compound of General Formula (II) is in cis configuration.

In particular, in this inhibitor compound of Formula (II), $R_6$ represents a preferably saturated, linear or branched-chain alkyl group, containing up to 5 carbon atoms. More preferably, in this inhibitor compound of Formula (II), $R_6$ represents a saturated linear chain alkyl group containing up to 5 carbon atoms. Even more preferably, in this inhibitor compound of Formula (II), $R_6$ represents a saturated linear chain alkyl group containing up to 3 carbon atoms.

In particular, in this inhibitor compound of Formula (II), $R_6$ represents a —($C_1$-$C_5$ alkyl)-aryl group, with said aryl being substituted by one or more groups, preferably a group, selected from the following groups: —$CO_2R_{11}$, $COR_{12}$, —$OC(O)R_{13}$, —$S(O)R_{14}$, —$OR_{15}$, —$SR_{16}$, —$SO_2R_{17}$, —$CONR_{18}R_{19}$, —$OCO_2R_{20}$. More preferably, in this inhibitor compound of Formula (II), $R_6$ represents a benzyl group, substituted by a group selected from the following groups: —$CO_2R_{11}$, —$COR_{12}$, —$OC(O)R_{13}$, —$S(O)R_{14}$, —$SO_2R_{17}$. With the groups $R_{11}$ to $R_{20}$ being as defined above. Even more preferably, in this inhibitor compound of Formula (II), $R_6$ represents a benzyl group, substituted by a carboxyl group.

Thus, particularly, the inhibitor compound according to the invention is selected from the group consisting of compounds of Formula (IIa), their salts, and/or solvates,

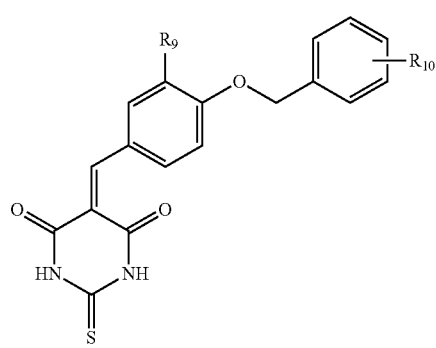

(IIa)

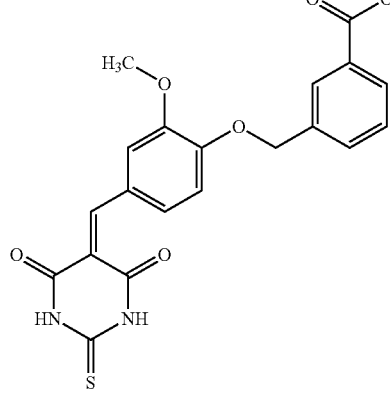

(IIc)

wherein:
the group $R_9$ represents a hydrogen atom or an alkoxyl group, and
the group $R_{10}$ represents a carboxylic group.

Preferably, in the inhibitor compound of Formula (II), the alkoxyl group of the group $R_9$ is selected from methoxyl or ethoxyl.

Preferably, in this inhibitor compound of Formula (II), the group $R_7$ represents a hydrogen atom when the group $R_8$ represents an aryl group.

Preferably, in this inhibitor compound of Formula (II), the group $R_8$ represents a hydrogen atom or a phenyl group.

In particular, the group $R_8$ represents a phenyl group. Thus, the inhibitor compound according to the invention is selected from the group consisting of compounds of Formula (IIb), their salts, and/or solvates,

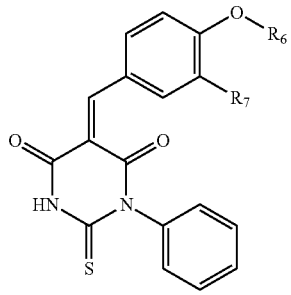

(IIb)

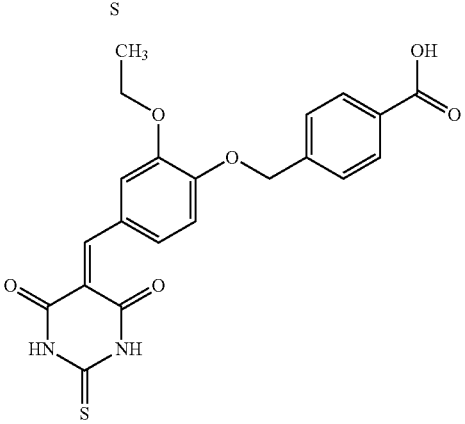

(IId)

(IIe)

wherein:
the group $R_6$ represents a linear or branched-chain alkyl group containing up to 5 carbon atoms, or a —($C_1$-$C_5$ alkyl) group, substituted by a carboxyl group, and
the group $R_7$ represents a hydrogen atom or a carboxyl group.

Even more preferably, especially in the context of use according to the present invention, the inhibitor compound is selected from the group consisting of compounds of Formula (IIc), (IId), (IIe), or (IIf).

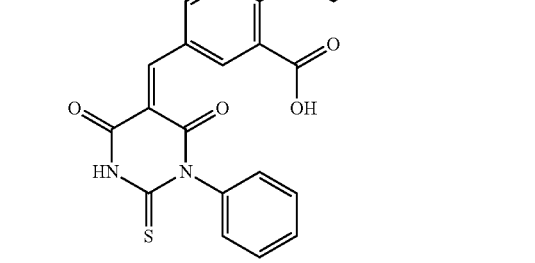

(IIf)

Pharmaceutical Composition

The invention also relates to a pharmaceutical composition comprising at least one inhibitor compound of Formula (I) or Formula (II) as defined above for its use for therapeutic purposes. In particular, the present invention also relates to a pharmaceutical composition comprising at least one inhibitor compound of Formula (I) or Formula (II) as defined above, and at least one pharmaceutically acceptable excipient for its use for therapeutic purposes.

The pharmaceutical compositions according to the invention may be formulated in particular for oral or parenteral administration, comprising subcutaneous, intravenous, and intramuscular administration, preferably for oral administration, said compositions being intended for mammals, including humans. Thus, the pharmaceutical composition can be, for example, administered orally by means of tablets and capsules.

When a solid composition is prepared in tablet form, the inhibitor compound according to the invention is mixed with a pharmaceutical carrier, such as gelatin, starch, lactose, magnesium stearate, talc, gum arabic, and the like. The tablets may be coated with sucrose or other suitable materials, or they may be processed in such a way as to have a prolonged or delayed activity and they continuously release a predetermined amount of active ingredient. Preparation in capsules is obtained by mixing the inhibitor compound according to the invention with a diluent and pouring the resulting mixture into soft or hard capsules.

For injection administration, aqueous suspensions, isotonic salt solutions, or sterile and injectable solutions containing pharmacologically compatible dispersants, and/or wetting agents are used.

According to a particular embodiment, the present invention relates to the inhibitor compound of General Formula (I) or (II) as defined above, or to a pharmaceutical composition according to the present invention, for use in the treatment of insulin resistance. Thus, this inhibitor compound according to the invention is particularly suitable for use as an insulin sensitizer.

The present invention also relates to the inhibitor compound of General Formula (I) or (II) as defined above, or to a pharmaceutical composition according to the present invention, for use in the prevention or treatment of a pathology associated with insulin resistance.

According to another particular embodiment, the present invention relates to a method for the treatment of insulin resistance comprising administering to a subject a pharmaceutically effective amount of an inhibitor compound of General Formula (I) or (II) as defined above or a pharmaceutical composition according to the present invention.

The present invention also relates to a method for preventing or treating a pathology associated with insulin resistance comprising administering to a subject a pharmaceutically effective amount of an inhibitor compound of the general Formula (I) or (II) as defined above or a pharmaceutical composition according to the present invention.

The present invention also relates to the use of an inhibitor compound of General Formula (I) or (II) as defined above, for the manufacture of a drug for the treatment of insulin resistance. In particular, the present invention also relates to the use of an inhibitor compound of General Formula (I) or (II) as defined above, for the manufacture of a drug for the prevention or treatment of a pathology associated with insulin resistance.

According to the invention, the pathology associated with insulin resistance may preferably be selected from: metabolic syndrome, polycystic ovary syndrome, obesity, pregestational diabetes, type 2 diabetes, hyperglycemia, lipodystrophy, diabetic nephropathy, or cardiovascular complications, such as high blood pressure, diabetic microangiopathy (including in particular diabetic neuropathy and diabetic retinopathy), or diabetic macroangiopathy.

More preferably, the pathology associated with insulin resistance can be preferably selected from: obesity, type 2 diabetes, metabolic syndrome, and hyperglycemia. Even more preferably, the pathology associated with insulin resistance can be preferably selected from: obesity, type 2 diabetes, and hyperglycemia.

In the context of the present invention, the inhibitor compound according to the invention may be administered in administration unit dosage forms, in admixture with conventional pharmaceutical carriers, to animals or mammals, preferably humans. The inhibitor compound of the invention as an active ingredient may be formulated in doses between 1 and 500 mg, preferably between 25 mg and 250 mg, even more preferably 50 mg and 150 mg in galenic forms allowing for administration in a single dose, twice daily in equal doses, or administration of the desired dose in a fractionated manner throughout the day (for example, but not only, in relation to meals). The dose administered daily is advantageously between 50 mg and 500 mg, preferably between 100 mg and 200 mg. The dose administered may also be indicated per unit of body weight of the patient to be treated, which is particularly relevant when treating a person whose body weight is outside the norm. Thus, the inhibitor compound of the invention as an active ingredient can be administered at daily doses between 1 and 40 mg/kg, preferably between 1 and 20 mg/kg, or even between 1 and 10 mg/kg. It may be necessary to use doses outside these ranges as defined above as determined by the one skilled in the art.

The administration of the inhibitor compound according to the invention may be performed at a rate of at least one administration per day. In some embodiments, the active ingredient may be administered at least once a week, for example twice a week. The treatment of insulin resistance or the prevention and treatment of a pathology associated with insulin resistance by administering the inhibitor compound according to the invention may be carried out for a period between 1 month and 96 months, preferably for a period between 6 months and 72 months, preferably for a period between 12 months and 48 months. The treatment of insulin resistance or the prevention and treatment of a pathology associated with insulin resistance by administering the active ingredient may also be extended for longer periods of time.

Although effective as such, the pharmaceutical compositions according to the invention may also comprise at least one other active ingredient, such as an active compound for the treatment of diabetes, and more particularly acting as an insulin secretion activator, insulin sensitizer, insulin effect potentiator, and/or carbohydrate gastrointestinal absorption inhibitor.

Thus, the present invention also relates to a pharmaceutical composition comprising:
(I) at least one inhibitor compound of Formula (I) or Formula (II) as defined above, and
(II) at least one other active ingredient, such as an anti-diabetic agent, preferably as a combination product for simultaneous, joint or separate, or sequential use.

The pharmaceutical composition according to the present invention may thus further comprise at least one other active ingredient selected from: sulfonylureas, biguanides, such as metformin, thiazolidinediones, GLP1 analogues, such as exenatide, or liraglutide, dipeptidyl peptidase-4 inhibitors, such as gliptin, sitagliptin, vildagliptin, saxagliptin, linagliptin, gemigliptin, or alogliptin, alpha-glucosidase inhibitors, glinides, fibrates, or SGLT2 inhibitors, such as canaglifozine.

Sulfonylureas are active ingredients used in the treatment of type 2 diabetes. They act by increasing the release of insulin from the beta cells of the pancreas. The sulfonylureas that can be used in combination with the inhibitor compound according to the invention can be more particularly selected from the following compounds: acetohexamide (968-81-0), carbutamide (339-43-5), chlorpropamide (94-20-2), glibenclamide (10238-21-8), glibornuride (26944-48-9), glipizide (29094-61-9), glimepiride (93479-97-1), gliclazide (21187-98-4), gliquidone (33342-05-1), glisentide (32797-92-5), glyclopyramide (631-27-6), tolbutamide (64-77-7), and tolazamide (1156-19-0).

Biguanides are active ingredients with antihyperglycemic properties taken orally used in the treatment of type 2 diabetes. The biguanides that can be used in combination with the inhibitor compound according to the invention can be more particularly selected from the following compounds: buformine (1190-53-0), metformin (657-24-9 or 1115-70-4), and phenformin (834-28-6).

Thiazolidinediones or glitazones are active ingredients allowing to reduce blood sugar levels and are used in the treatment of type 2 diabetes. The thiazolidinediones that can be used in combination with the inhibitor compound according to the invention can be more particularly selected from the following compounds: rosiglitazone (122320-73-4 or 302543-62-0 or 155141-29-0 or 397263-60-4), and pioglitazone (111025-46-8 or 112529-15-4).

Glucagon-like peptide-1 (GLP1) analogues promote the proliferation of β cells, inhibit the apoptosis of β cells, and are used in the treatment of type 2 diabetes. The GLP1 analogues that can be used in combination with the inhibitor compound according to the invention can be more particularly selected from the following compounds: exenatide (141758-74-9) and liraglutide (204656-20-2).

Dipeptidyl peptidase-4 inhibitors allow for an increase in insulin secretion, a decrease in glucagon secretion, and are thus used in the treatment of type 2 diabetes. The dipeptidyl peptidase-4 inhibitors that can be used in combination with the inhibitor compound according to the invention can be more particularly selected from the following compounds: alogliptin (850649-62-6), sitagliptin (654671-78-0), vildagliptin (274901-16-5), saxagliptin (361442-04-8), linagliptin (668270-12-0), gemigliptin (911637-19-9), berberine (2086-83-1 or 633-65-8 or 633-66-9), and dutogliptin (852329-66-9).

Alpha-glucosidase inhibitors allow to reduce postprandial hyperglycemia and are therefore used in the treatment of type 2 diabetes. The alpha-glucosidase inhibitors that can be used in combination with the inhibitor compound according to the invention can be more particularly selected from the following compounds: acarbose (56180-94-0), miglitol (72432-03-2), and voglibose (83480-29-9).

SGLT2 (sodium-glucose type 2 co-transporter) inhibitors allow to improve insulin sensitivity and ß-cellular function. The SGLT2 inhibitors that can be used in combination with the inhibitor compound according to the invention can be more particularly selected from the following compounds: canaglifozine(842133-18-0), dapagliflozine(461432-26-8), ipragliflozine (761423-87-4), tofogliflozine (1201913-82-7 or 903565-83-3), and empagliflozine (864070-44-0).

Glinides improve insulin secretion and are used in the treatment of type 2 diabetes. The glinides that can be used in combination with the inhibitor compound according to the invention can be more particularly selected from the following compounds: mitiglinide (145375-43-5), nateglinide (105816-04-4), and repaglinide (135062-02-1).

Fibrates are lipid-lowering compounds. The fibrates that can be used in combination with the inhibitor compound according to the invention can be more particularly selected from the following compounds: bezafibrate (41859-67-0), ciprofibrate (52214-84-3), clofibrate (637-07-0 or 882-09-7 or 39087-48-4 or 14613-30-0), fenofibrate (49562-28-9 or 42017-89-0 or 856676-23-8), and gemfibrozil (25812-30-0).

Preferably, the pharmaceutical composition according to the invention also comprises at least one other active ingredient selected from: metformin, gliptin, and canaglifozine.

The invention also relates to a pharmaceutical composition according to the invention, for its use for therapeutic purposes in a subject subjected to insulin therapy, said insulin therapy comprising the administration of insulin or an insulin analogue.

For example, the insulin analogue may be an insulin modified to change the rate at which it is absorbed by the subject. Commercial products are, for example, Lispro, Aspart, Glulisine, Detemir, Degludec, and Glargine.

The present invention also relates to a method for treating insulin resistance, and more particularly for preventing or treating a pathology associated with insulin resistance, comprising the administration to a subject in need thereof of a pharmaceutically effective amount of the pharmaceutical composition as defined above.

The present invention also relates to the use of the pharmaceutical composition as defined above for the manufacture of a drug for the treatment of insulin resistance. In particular, the present invention also relates to the use of the pharmaceutical composition as defined above, for the manufacture of a drug for the prevention or treatment of a pathology associated with insulin resistance.

Synthesis of the Inhibitor Compound According to Formula (I)

According to another aspect, the invention relates to a method for synthesizing a compound of Formula (I) as defined above and including the preferred embodiments. Where said method comprises a step of condensing a sulfonamide of Formula (V)

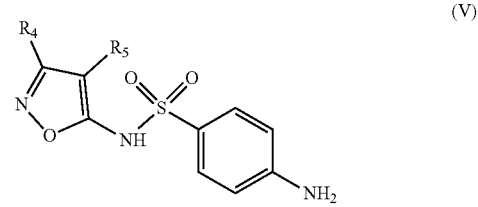

wherein:
the groups $R_4$ and $R_5$ are identical or different and represent a hydrogen atom or a linear, cyclic or branched-chain alkyl group containing up to 5 carbon atoms;
with an acrylic acid derivative of Formula (IV)

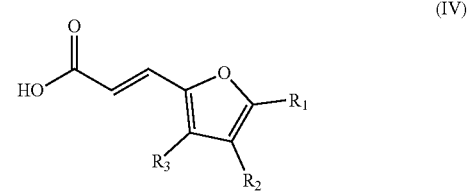

wherein:
the group $R_1$ represents a linear, cyclic or branched-chain alkyl group containing up to 5 carbon atoms, and
the groups $R_2$ and $R_3$ are identical or different and represent a hydrogen atom or a linear, cyclic or branched-chain alkyl group containing up to 5 carbon atoms.

The acrylic acid derivative of Formula (IV) can easily be purchased commercially or synthesized from the general knowledge of the one skilled in the art, or from the teachings of Pontiki et al. (2011). In particular, the synthesis method according to the invention may comprise a preliminary step of condensing an aldehyde of Formula (III)

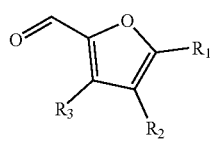

(III)

wherein:
the group $R_1$ represents a linear, cyclic or branched-chain alkyl group containing up to 5 carbon atoms, and
the groups $R_2$ and $R_3$ are identical or different and represent a hydrogen atom or a linear, cyclic or branched-chain alkyl group containing up to 5 carbon atoms;
with a malonic acid in the presence of pyridine and piperidine.

The condensation reaction of the sulfonamide of Formula (V) with the acrylic acid derivative of Formula (IV) is difficult to achieve because of the low reactivity of the sulfonamide of Formula (V) and the presence of two potentially nucleophilic sites on this molecule.

In the previous art, it is proposed to react a sulfamide (not of Formula (V)) with an acyl chloride derivative (Marwaha et al, 2014). Nevertheless, reproducing this protocol with a sulfonamide of Formula (V) and an acyl chloride derivative corresponding to an acrylic acid derivative of Formula (IV) does not yield a compound of Formula (I). Indeed, as mentioned in the examples, this protocol leads to the generation of a heterogeneous reaction mixture unable to allow for the synthesis of a compound of Formula (I).

In addition, an improvement of this protocol according to the teachings of document U.S. Pat. No. 3,427,318 allows to achieve a complex crude from which, as presented in the examples, it is possible to purify a compound of Formula (I) with 11% yield only. Thus, the protocols of the prior art, in particular those based on Marwaha et al., 2014, even modified, do not allow the production of a compound of Formula (I) with a satisfactory yield.

The inventors of the present invention have therefore defined reaction conditions for obtaining satisfactory condensation yields at the desired nucleophilic site. This involves, in particular, the use of an acrylic acid derivative of Formula (IV) instead of an acyl chloride derivative.

In addition, preferably, the condensation reaction of a sulfonamide of Formula (V) with an acrylic acid derivative of Formula (IV) is carried out in the presence of a peptide coupling reagent.

Preferably, the peptide coupling reagent is selected from HATU (1-[Bis(dimethylamino)methylene]-1H-1,2,3-triazolo[4,5-b]pyridinium 3-oxide hexafluorophosphate) and Ghosez's reagent (1-Chloro-N,N,2-trimethylpropenylamine). The coupling reagent may also be used in combination with DIPEA (N-Ethyl-N-(propan-2-yl)propan-2-amine).

Preferably, the step of condensing the sulfonamide of Formula (V) with the acrylic acid derivative of Formula (IV) is carried out in the presence of DMF (Dimethylformamide) or DCM (Dichloromethane), more preferably in the presence of DMF.

Preferably, the step of condensing the sulfonamide of Formula (V) with the acrylic acid derivative of Formula (IV) comprises a step of heating and microwave irradiating, for example at 70° C. and 40 W.

As for the compounds according to Formula (II), they can be easily purchased commercially or synthesized by methods known from prior art, such as that described in Uciechowska et al. (2008).

The present invention will be better understood in the light of the following examples illustrative of the invention.

EXAMPLES

The following abbreviations have been used in the following examples.
BRET: Bioluminescence resonance energy transfer
DCM: Dichloromethane
DIPEA: N,N-Diisopropylethylamine
DMF: Dimethylformamide
DMSO: Dimethylsulfoxide
EDCI: 1-Ethyl-3-(3-dimethylaminopropyl)carbodiimide
HATU: 1-[Bis(dimethylamino)methylene]-1H-1,2,3-triazolo[4,5-b]pyridinium 3-oxide hexafluorophosphate
HOBt: Hydroxybenzotriazole
HPLC: High Performance Liquid Chromatography
IBCF: Isobutylchloroformate
IR: Insulin receptor
Luc: Luciferase
μW: Microwave
NMR: Nuclear Magnetic Resonance
THF: Tetrahydrofuran
rt: room temperature
YFP: Yellow Fluorescent Protein Example 1

Synthesis of Sulfonamide Isoxazoles of Formula (I)

1.1 Preliminary Step of Forming the Compound of Formula (IV)

The first optional step consists in the transformation of an aldehyde of Formula (III), such as 5-methyl-2-furfuraldehyde into an acrylic acid derivative of Formula (IV), such as (E)-3-(5-methylfuran-2-yl)acrylic acid. This transformation has already been described in the literature (Pontiki et al., 2011). In short (E)-3-(5-methylfuran-2-yl)acrylic acid was obtained by condensing 5-methyl-2-furfuraldehyde with malonic acid in the presence of pyridine and piperidine.

1.2 Step of Forming the Compound of Formula (I)

The second step consists in the condensation of a sulfonamide of Formula (V), such as 4-amino-N-(3,4-dimethyl-1,2-oxazol-5-yl)benzenesulfonamide (sulfisoxazole) with an acrylic acid derivative of Formula (IV), such as (E)-3-(5-methylfuran-2-yl)acrylic acid, in the presence of a peptide coupling reagent.

Synthesis of the Compound of Formula (Ia):

In a microwave reactor (volume 10 mL), a solution of (E)-3-(5-methylfuran-2-yl)acrylic acid (76 mg; 0.5 mmol) in anhydrous DMF (0.625 mL), under argon, at 0° C., is treated with HATU (190 mg; 0.5 mmol), and then DIPEA (87 μL; 0.5 mmol). The mixture is stirred for 5 minutes at 0° C. Sulfisoxazole (134 mg; 0.5 mmol) is then added and the mixture is stirred at room temperature for 15 minutes, and then irradiated with microwaves (70° C.; 40 W) for 25 minutes. The mixture is treated with EtOAc (100 mL) and extracted with a saturated aqueous solution of NaHCO$_3$ (50 mL).

The aqueous extract is acidified with 6M HCl (6 mL) to acid pH. The thus formed precipitate is filtered on a Buchner, rinsed with distilled water (2×5 mL), and dried at 40° C. for 6 h to give the compound of Formula (Ia) (89 mg; 44%) in the form of a light-yellow solid.

Analysis of the Compound of Formula (Ia):

Purity >95% by inspection of the $^1$H NMR spectrum; R$_f$=0.33 (EtOAc); F=150-151° C.; IR (ATR): ν3315, 3112, 3060, 2839, 2774, 1673, 1625, 1589, 1540, 1526, 1497, 1419, 1368, 1334, 1348, 1253, 1189, 1162 cm$^{-1}$; $^1$H NMR (250 MHz, DMSO-d$_6$) : δ 10.95 (1H, bs, H6), 10.60 (1H, s, H12), 7.88 (2H, d, J=9.0 Hz, H9), 7.72 (2H, d, J=9.0 Hz, H10), 7.37 (1H, d, J=15.5 Hz, H14), 6.80 (1H, d, J=3.3 Hz, H17), 6.37 (1H, d, J=15.5 Hz, H15), 6.28 (1H, d, J=3.3 Hz, H18), 2.35 (3H, s, H23), 2.10 (3H, s, H21), 1.63 (3H, s, H22) ; $^{13}$C NMR (75 MHz, DMSO-d$_6$): δ 164.2 (C13), 161.4 (C5), 155.6 (C3), 154.9 (C19), 149.4 (C16), 143.7 (C11), 133.5 (C8), 128.2 (C14), 128.0 (C9), 118.8 (C10), 117.1 (C15), 116.9 (C17), 109.2 (C18), 105.1 (C4), 13.5 (C23), 10.3 (C21), 5.8 (C22) ; SMHR: m/z found: 424.0925 [M+Na]$^+$; calculated for C$_{19}$H$_{19}$N$_3$NaO$_5$S: 424.0938.

1.2: Optimization of the Synthesis Conditions

The condensation reaction of a sulfonamide of Formula (V) with an acrylic acid derivative of Formula (IV) is difficult to achieve because of the low reactivity of the sulfonamide of Formula (V) coupled with the presence of two potentially nucleophilic sites. Different methods of synthesis of the compound of Formula (I) were assessed in order to compare the synthesis yields of the compound of Formula (I) from (E)-3-(5-methylfuran-2-yl)acrylic acid and sulfisoxazole under the coupling conditions.

As shown in Table 1, depending on the reaction conditions and coupling reagent used, the synthesis yield of the compound of Formula (Ia) varies from 17 to 44%.

TABLE 1

| Conditions | Yield of Formula (Ia) |
|---|---|
| HATU, DIPEA, DMF, μW, 70° C., 25 min | 44% |
| HATU, DIPEA, DMF, rt, 48 h | 28% |
| EDCI, HOBt, Et$_3$N, THF, rt, 48 h | 25% |
| EDCI, DIPEA, DMF, rt, 48 h | 17% |
| IBCF, DIPEA, DMF, μW, 70° C., 25 min | 19% |
| Ghosez reagent, DIPEA, DCM, rt, 72 h | 32% |
| Pyridine, rt, 18 h[a][b] | 0% |
| Pyridine, acetone, 4° C., 30 min, and then reflux, 30 min[a][c] | 11% |

[a](E)-3-(5-Methylfuran-2-yl)acryloyl chloride was used instead of (E)-3-(5-methylfuran-2-yl)acrylic acid.
[b]Following the protocol described by S. Marwaha et al. 2014. The reaction mixture was heterogeneous.
[c]Following the protocol described by M. S. Barber et al., U.S. Pat. No. 3,427,318 (1969).

Thus, it appears from these experiments that the inventors have identified conditions allowing high yields of inhibitor compounds of Formula (I), and more particularly of inhibitor compounds of Formula (Ia or Ib), to be achieved.

For example, associated with DIPEA, HATU and Ghosez's reagent appear to be the peptide coupling reagents that provide the best yields in these synthesis experiments. Similarly, DMF and DCM solvents allow the highest yields to be achieved, especially when using microwave irradiation.

On the contrary, the results obtained when using an acyl chloride derivative as suggested in the previous art allow at best to obtain a reaction crude comprising very many very largely degraded compounds where the compound of Formula (I) represents less than 15%. Thus, if acyl chloride is the most obvious choice that seems to be the fastest and simplest for the one skilled in the art, it turns out that for the synthesis of compounds of Formula (I), it is too reactive and not selective enough.

Example 2

Assessment of the Inhibitory Effect of the Compounds According to Invention by a Cell-Free BRET Method Compounds according to the invention were experimentally assessed for their inhibitory effect on the IR-Grb14 interaction by a BRET technique in a cell-free system described briefly below.

On the one hand, HEK293T cells were transfected with a vector encoding the insulin receptor fused to the luciferase (IR-Luc). Before lysis, the cells transfected with IR-Luc were stimulated or not with 100 nM insulin for 10 minutes. The IR-Luc lysates were recovered and then purified on sepharose beads coupled with wheat germ lectin (WGL for Wheat Germ Lectin). The IR-Luc receptors were then eluted and then frozen in liquid nitrogen before being stored at −80° C. On the other hand, HEK293T cells were transfected either with a vector encoding the Grb14 protein fused to the YFP (Grb14-YFP), or with the empty plasmid pcDNA3. The cells transfected with Grb14-YFP or with the empty plasmid pcDNA3 were lysed 48 h after transfection. After centrifugation, the lysates are recovered and frozen at −80° C.

The insulin receptors (IR-Luc) partially purified from cells stimulated or not with insulin were incubated for 20 minutes with the inhibitor compounds according to the invention suspended in DMSO. The cellular extracts from cells transfected with Grb14-YFP (or the empty plasmid pcDNA3) were then added and then after 40 minutes of incubation, coelenterazine was added and BRET reading was initiated. The results are expressed as a percentage of the BRET signal obtained in the presence of the molecules tested compared to the BRET signal of the DMSO control.

The results of this assessment are illustrated in the case of the compound of Formula (Ia) according to the invention in FIG. 1 and reported in Table 2 below in the case of the other compounds according to the invention in the presence of insulin stimulation (100 nM).

TABLE 2

| Compound assessed (50 μM) | % BRET signal/DMSO control |
|---|---|
| Ia | 39% (+/−16%) |
| Ib | 58% (+/−12%) |
| IIc | 75% (+/−13%) |
| IId | 69% (+/−18%) |
| IIe | 65% (+/−20%) |
| IIf | 65% (+/−7%) |
| Comparative IVa | 91% (+/−12%) |
| Comparative Va | 98% (+/−5%) |
| Comparative IVa + Va | 98% (+/−8%) |
| Comparative A | 103% (+/−15%) |
| Comparative B | 93% (+/−7%) |
| Comparative C | 103% (+/−8%) |
| Comparative D | 121% (+/−8%) |
| Comparative E | 98% (+/−9%) |
| Comparative F | 93% (+/−24%) |

The compounds according to the invention induce a decrease in the BRET signal between the insulin receptor and the Grb14 protein. For example, at a concentration of 50 µM, the compound of Formula IIc decreases by 25% the BRET signal between the insulin receptor and the Grb14 protein. As for the compound of Formula (Ia), it induces a significant 60% decrease in IR-Grb14 BRET at 50 µM.

In addition, as shown in FIG. 1, a significant 50% decrease in the BRET signal by the compound of Formula (Ia) is also observed in the absence of stimulation with insulin. In addition, additional studies have confirmed, for the compounds according to the invention, the presence of a dose-response effect on the reduction of the BRET signal.

On the contrary, some compounds sharing structural similarities with the compounds according to the invention fail to induce a significant decrease in the BRET signal between the insulin receptor and the Grb14 protein.

For example, the activity of the compounds (IVa) and (Va) used in the synthesis of the compound of Formula (Ia) was tested via the BRET technique in a cell-free system detailed above. The compounds of Formula (IVa) and (Va) taken individually, added separately or simultaneously, do not allow for a reduction in the IR-Grb14 interaction. Thus, the inhibitory activity of the compound of Formula (Ia) is therefore not dependent on a partial structure of this compound, and the molecule is required in its entirety.

Moreover, as detailed in Table 2, Compounds A and B structurally close to the compounds of Formula (Ia) or (Ib), do not allow for a significant decrease in the BRET signal. In addition, these comparative tests show the importance to the compounds of General Formula (I) of the furan ring (see Comparative Compound B), as well as the substituent in the $R_1$ position (see Comparative Compound A).

Similarly, as detailed in Table 2, Compounds C, D, E and F structurally close to the compounds of General Formula (II) do not allow for a significant decrease in the BRET signal. These results confirm the need for a substituent on the aryl in $R_6$ (see Comparative Compound C), in addition this substituent is nucleophilic (see Comparative Compound D) without being a halogen (see Comparative Compound E). These results also show the importance of the presence of a carbon atom bonded to a sulfur atom in position 2 of the pyrimidine ring (see Comparative Compound F).

Compound IVa

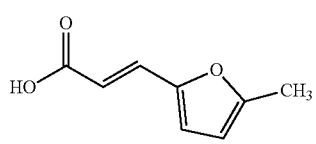

Compound Va

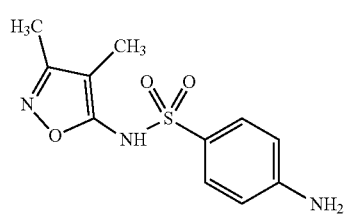

Comparative Compound A

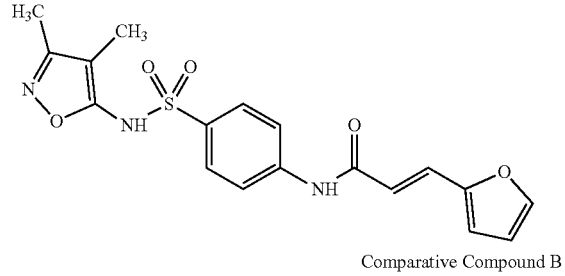

Comparative Compound B

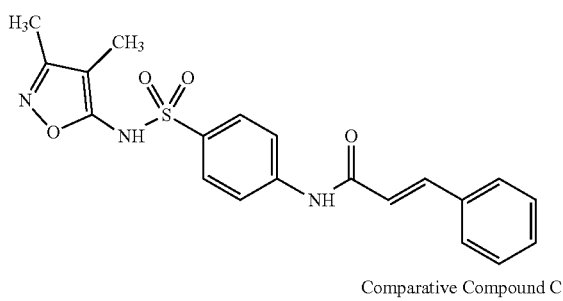

Comparative Compound C

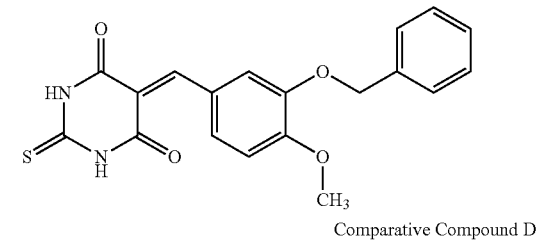

Comparative Compound D

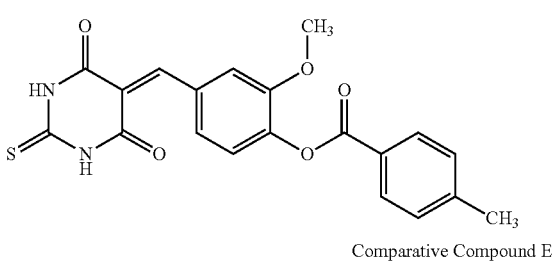

Comparative Compound E

Comparative Compound F

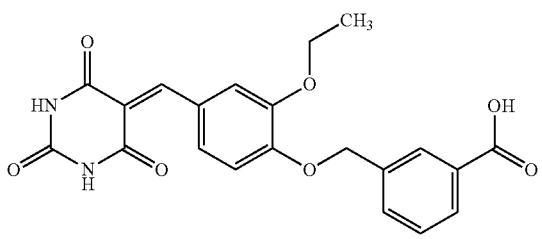

Example 3

Validation of the Inhibitory Effect by a Co-Immunoprecipitation Method

The inhibitory effect of the compounds according to the invention on the IR-Grb14 interaction has been confirmed in co-immunoprecipitation experiments in a cell-free system. IR-Luc extracts, stimulated or not by insulin, were pre-incubated for 20 minutes in the absence or presence of 50 µM of the compound according to the invention before being incubated with the cellular extract containing the fusion protein Grb14-YFP for 40 minutes. Immunoprecipitation against YFP allows to analyze by Western blot the amount of receptor that has remained associated with the Grb14 protein.

As expected, the association between IR and Grb14 proteins is much more important with receptors from insulin-stimulated cells than with receptors from cells not stimulated by the hormone (FIG. 2). It is observed that the compound of Formula (Ia) according to the invention reduces by 60% the amount of insulin receptors associated with the Grb14 protein in the presence of insulin. Finally, co-immunoprecipitation experiments in a cell-free system also show dose-dependent inhibition by the compound of Formula (Ia), of the amount of IR immunoprecipitated with Grb14. Indeed, in this series of experiments, the amount of co-precipitated IR-Luc is reduced by 20% at a concentration of 25 µM and by 50% at a concentration of 50 µM (results not shown).

Example 4

Specificity of the Action of the Compounds According to the Invention 4.1: Specific action on the TK (tyrosine kinase) domain of the insulin receptor HEK 293T cells co-transfected with a construct bearing only the tyrosine kinase domain of the luciferase-fused receptor (IRTK48-RLuc) and the Grb14 protein fused to YFP were incubated for 4 hours in the presence of compounds according to the invention. In the absence of α subunits, the tyrosine kinase domain of the insulin receptor spontaneously autophosphorylates, so it is not necessary to add insulin to stimulate the IRTK-Grb14 interaction.

Western blot analysis of the amount of IRTK48-Rluc co-precipitated with Grb14 proteins (FIG. 3A) shows that the amount of tyrosine kinase domain of the insulin receptor co-immunoprecipitated with the Grb14 protein is reduced by 75% by the compound of Formula (Ia), 50 µM. This result indicates that the compound of Formula (Ia) enters the cells and decreases the interaction between the kinase domain of the insulin receptor and the Grb14 protein. The compound of Formula (Ia) therefore acts indeed at the level of the tyrosine kinase domain of the insulin receptor, the only part of the receptor present in the construct used for this experiment. This confirms that the compounds according to the invention inhibit the IR-Grb14 interaction by acting specifically on the kinase domain of the insulin receptor.

4.2: Specific Action on Grb14

In order to test the specificity of the compound of Formula (Ia) on this IRTK-Grb14 interaction, the same experiment was conducted with HEK 293T cells co-transfected with a construct bearing only the tyrosine kinase domain of the luciferase-fused receptor and the Grb10 protein fused to YFP. Indeed, the Grb10 protein also binds to the phosphorylated insulin receptor and inhibits its catalytic activity.

FIG. 3B, showing the densitometric quantification of the revealed signals, shows that the compound of Formula (Ia) does not change the amounts of tyrosine kinase domain of the insulin receptor co-immunoprecipitated with the Grb10 protein. Thus, the compound of Formula (Ia) appears to be specific to the IRTK-Grb14 interaction, since it does not inhibit the IRTK-Grb 10 interaction.

Example 5

Absence of Toxicity of the Compounds According to the Invention 5.1: Toxicity on HEK293T cells In order to study the effect of the compound of Formula (Ia) on cell growth and survival, HEK293T cells were cultured for 72 h at different serum concentrations (0.1%, 1%, 10%), in the absence or presence of compounds of Formula (Ia) (50 or 100 µM). The fluorescence of the cells was measured before and after treatment using a reagent containing resazurin. Since the intensity of fluorescence is correlated with the number of living cells, cell growth is estimated by relating the fluorescence measured at 72 h of treatment to that measured at t0. The presence of serum promotes cell growth. Thus, after 72 h, an increase in the cell population of 7 times at 0.1% of serum and of 10 times at 1 or 10% of serum is observed.

As shown in FIG. 4, whether at a low serum concentration of 0.1% (to measure cell survival) or at a high serum concentration of 10% (to measure cell proliferation), the compound of Formula (Ia) at 50 µM and 100 µM does not alter cell growth rate.

5.1: In Vivo Toxicity

A repeat-dose toxicity study was also conducted in C57Bl/6J mice (12 males, 8 weeks old). Mice were treated daily either by gavage with 30 mg/kg/day of compound of Formula (Ia) diluted in 0.5% carboxymethylcellulose; or by intraperitoneal injection with 30 mg/kg/day of compound of Formula (Ia) diluted in DMSO, or with DMSO alone, for a period of 15 days.

Before starting the treatments, the mice had a similar body weight. After 12 days of treatment, no difference in weight gain was observed between the different groups, regardless of the treatment. In addition, regardless of the administration mode of the compound according to the invention, it is possible to observe a decrease in blood glucose level measured in the post-absorptive state. Finally, no difference in liver appearance was observed in these mice.

The compound of Formula (Ia) according to the invention therefore has no detectable toxic effect.

Example 6

Activation of the PI3-Kinase Pathway by the Compounds According to the Invention 6.1: Recruitment of the Akt Protein to the Membrane To measure the activity of the PI3-kinase pathway by the BRET technique, HEK293T cells are transfected with plasmids allowing, on the one hand, the expression of the PH (Pleckstrin Homology) domain of the Akt protein which has been fused to the luciferase and, on the other hand, a membrane-addressing sequence which has been fused to the YFP protein. When the PH domain of Akt is recruited to the membrane by the PIP3s, an energy transfer between the luciferase that is coupled to the PH domain of Akt and the membrane YFP protein takes place. The measured BRET signal is a control of the production of PIP3s at the membrane and is a reflection of the activation of the PI-3-kinase/Akt pathway in real time on cells.

The results of this evaluation are illustrated in the case of the compound of Formula (Ia) according to the invention in FIG. 5 and reported in Table 3 below in the case of the other compounds according to the invention.

TABLE 3

|  | BRET delta |
| --- | --- |
| IId† | 67 (+/−33) |
| IIe† | 96 (+/−50) |
| IIf† | 54 (+/−44) |
| Ia† | 86 (+/−41) |
| Ib† | 119 (+/−26) |
| Comparative Compound IVa* | −61 (+/−35) |
| Comparative Compound Va* | −27 (+/−23) |
| Comparative Compound IVa + Va* | −75 (+/−14) |

*in the presence of insulin;
†without insulin

As shown in FIG. 5A, insulin (5 nM) induces a rapid increase in the BRET signal (BRET delta of about 100). The compound of Formula (Ia) (50 µM) increases the recruitment of the Akt protein to the membrane in the absence (BRET delta of about 86) and in the presence (BRET delta of about 121) of 5 nM insulin. The more concentrated the compound of Formula (Ia) is, the more the production of PIP3s at the membrane is increased. In addition, the effect of the compound of Formula (Ia), in the absence of insulin, is detectable from 5 µM, with a significant increase in the BRET signal at 10 µM (results not shown). This effect is also observed for the other inhibitor compounds according to the invention as presented in Table 3.

Inhibition of tyrosine kinase activity of the insulin receptor in this system, by pre-incubating cells for 1 h with 25 µM tyrosine kinase inhibitor AG1024, results in a very significant drop in the BRET signal. Insulin (5 nM) and the compound of Formula (Ia) (50 µM) no longer have any effect on the recruitment of the Akt protein to the membrane (FIG. 5A).

In the same way as before, the effect of the comparative compounds of Formula (IVa) and Formula (Va) used in the synthesis of the compound of Formula (Ia) on the PI3K/Akt pathway was tested in the presence of 5 nM insulin. Unlike the compound of Formula (Ia), the compounds of Formula (IVa) and Formula (Va) (added separately or simultaneously) have no effect on the recruitment of kinase Akt to the membrane in the absence of the hormone. In addition, in the presence of insulin, the compound of Formula (Va) also has no effect on the production of PIP3s at the membrane. As for the compound of Formula (IVa), it alone reduces the recruitment of the Akt protein to the membrane by about 50% and by at least 60% when combined with the compound of Formula (Va).

In addition, as shown in FIG. 5B, the effect of the compound of Formula (Ia) on the increase of the production of PIP3s at the membrane was not found in all cellular systems. Indeed, in MCF7 cells (mammary tumor cells) overexpressing the IGF-1 receptor with respect to the insulin receptor (Zhang et al., 2007), the compound of Formula (Ia) (50 µM) has no effect on the production of PIP3s at the membrane (in the absence and presence of 100 nM insulin). This suggests that the compound of Formula (Ia) does not stimulate the PI3K/Akt pathway in cancer cells overexpressing the IGF-1 receptor. Finally, the compounds according to the invention increase the Ras/Raf interaction whether the cells are stimulated by insulin or not (results not shown).

The compounds according to the invention therefore induce an activation of the PI3K/Akt pathways. These compounds potentiate the effect of insulin, but also have an activating effect in the absence of the hormone. In addition, the effect of the compound of Formula (Ia) on the activation of the PI3K/Akt pathway is significant from 10 µM. Finally, the effect of the compound of Formula (Ia) on the activation of the PI3K/Akt pathway depends on the TK activity of the insulin receptor, demonstrating specificity of action.

6.2: Expression of Neoglucogenesis Genes

To study the inhibitory effect of insulin on neoglucogenesis gene expression, hepatocytes from mice in primary culture were pre-incubated with 10 nM glucagon.

As shown in FIG. 6, glucagon strongly induces the expression of the key genes of neoglucogenesis that are PEPCK and G6Pase, and the addition of 1 nM insulin inhibits by about 60 to 70% the expression of these genes. The compound of Formula (Ia) induces a significant decrease of about 20% in glucagon-induced PEPCK and G6Pase expression. Thus, the compounds according to the invention also decrease, even in the absence of insulin, the expression of glucagon-induced neoglucogenesis genes in hepatocytes in primary culture.

6.3: Expression of Lipogenesis Genes

The stimulation of lipogenesis in response to insulin occurs at the transcriptional level, in particular through the activation of the transcription factor SREBP-1c (Sterol Regulatory Element Binding Protein 1c). This transcription factor, once activated and cleaved, migrates into the nucleus and regulates the expression of key lipogenesis enzymes (ACC, FAS, and SCD1).

Briefly, mouse hepatocytes in primary culture are cultured in the presence of 5 mM glucose (G5) or 25 mM glucose (G25), and 10 nM insulin for 24 h. The relative quantification of mRNAs is performed by RT-qPCR and the values are related to the quantification of the 18S gene from the same sample in order to normalize the results.

As shown in FIG. 7, under condition G25i (G25, with 10 nM insulin), a 60% increase in the expression of the SREBP-1c messenger RNA, as well as an increase in the expression of its target genes ACC (by 650%), FAS (by 150%), and SCD1 (by 160%), were observed. Interestingly, the addition of the compound of Formula (Ia) under condition G25i enhances the effect of insulin on the expression of these genes. The effect of the hormone on the expression of SREBP-1c and its target genes ACC, FAS, and SCD1, is thus increased by about 60%. Thus, there is a potentiation of the effect of insulin on lipogenesis by the compounds according to the invention.

These examples, without limiting the invention, confirm that the compounds according to the invention significantly decrease the IR-Grb14 interaction in a reproducible way. Nontoxic, these compounds penetrate membranes and stimulate the PI3K/Akt and MAP kinase pathways. They also increase PIP3 production and activate the Ras/Raf channel in the basal state. Finally, they improve the effect of insulin in hepatocytes from mice in primary culture, potentiating in particular the effect of insulin on the expression of lipogenesis and neoglucogenesis genes. Thus, by decreasing the IR-Grb14 interaction, the compounds according to the invention increase insulin signaling and are promising compounds for therapeutic use, especially for the treatment of insulin resistance.

REFERENCES

B. Desbuquois, N. Carré, A. F. Burnol. Regulation of insulin and type 1 insulin-like growth factor signaling and action by the Grb10/14 and SH2B1/B2 adaptor proteins. FEBS J. 2013 February; 280(3):794-816. doi: 10.1111/febs.12080.

Lowenna J. Holt and Kenneth Siddle. Grb10 and Grb14: enigmatic regulators of insulin action—and more? Biochem J. 2005 Jun. 1; 388(Pt 2): 393-406.doi: 10.1042/BJ20050216.

Andy Menke et al. Prevalence of and Trends in Diabetes Among Adults in the United States, 1988-2012. *JAMA*. 2015; 314(10):1021-1029. doi:10.1001/jama.2015.10029.

Expert panel on detection, evaluation and treatment of high blood cholesterol in adults. Executive summary of the third report on the National cholesterol education program (NCEP) expert panel on detection, evaluation and treatment of high blood cholesterol in adults (Adult treatment panel III). JAMA 2001; 285: 2486-97.

P. H Stahl, C. G. Wermuth. Pharmaceutical Salts: Properties, Selection, and Use. Wiley, 2011. 388 pages.

S. Marwaha et al. N-Acylated Derivatives of Sulfamethoxazole and Sulfafurazole Inhibit Intracellular Growth of Chlamydia trachomatis. Antimicrob Agents Chemother. 2014 May; 58(5):2968-71. doi: 10.1128/AAC.02015-13.

E. Pontiki, D. Hadjipavlou-Litina, K. Litinas, O. Nicolotti, A. Carotti (2011) Design, synthesis and pharmacobiological evaluation of novel acrylic acid derivatives acting as lipoxygenase and cyclooxygenase-1 inhibitors with antioxidant and anti-inflammatory activities. European journal of medicinal chemistry 46:191-200

U. Uciechowska, J. Schemies, R. C. Neugebauer, E. M. Huda, M. L. Schmitt, R. Meier, E. Verdin, Manfred Jung, and W. Sippl. Thiobarbiturates as Sirtuin Inhibitors: Virtual Screening, Free-Energy Calculations, and Biological Testing. ChemMedChem 2008, 3, 1965-1976

World Health Organization. Definition, diagnosis and classification of diabetes mellitus and its complications. Classification of diabetes mellitus and its complications. Report of a WHO consultation 1999.

P. Zimmet, G. Alberti, J. Shaw. Nouvelle définition globale du syndrome metabolique raisonnement et résultats. Diabetes'Voice 2005; 50:3 31-33.

The invention claimed is:

1. A method for treatment of insulin resistance and/or prevention and/or treatment of a pathology associated with insulin resistance, comprising administering to a patient in need thereof a compound inhibiting interaction between a Grb14 protein and an insulin receptor, said compound being selected from the group consisting of compounds belonging to the family of sulfonamide isoxazoles of Formula (I), and salts, solvates, and/or diastereoisomers thereof:

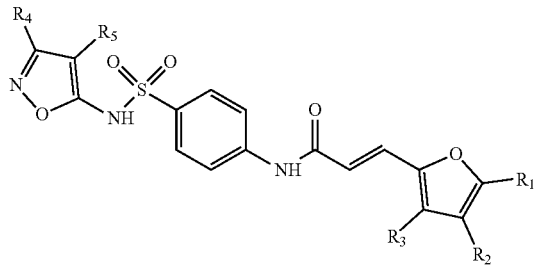

Formula (I)

wherein:
the group $R_1$ represents a linear, cyclic or branched-chain alkyl group containing up to 5 carbon atoms, and the groups $R_2$, $R_3$, $R_4$, and $R_5$ are identical or different and represent a hydrogen atom or a linear, cyclic or branched-chain alkyl group containing up to 5 carbon atoms.

2. The method according to claim 1, said compound being of Formula (I) in a trans configuration.

3. The method according to claim 1, said compound being of Formula (I) wherein the groups $R_2$ and $R_3$ represent a hydrogen atom.

4. The method according to claim 1, said compound being of Formula (I) wherein the groups $R_4$ and $R_5$ represent a methyl group.

5. The method according to claim 1, said compound being of Formula (I) wherein the group $R_1$ represents a saturated linear or branched-chain alkyl group containing up to 5 carbon atoms.

6. The method according to claim 1, said compound being of Formula (I) wherein:

the group $R_1$ represents a linear or branched-chain alkyl group containing up to 5 carbon atoms, the groups $R_2$ and $R_3$ represent a hydrogen atom, and the groups $R_4$ and $R_5$ represent a methyl group.

7. The method according to claim 1, wherein said compound is selected from the group consisting of compounds of Formula (Ia), Formula (Ib), and salts, solvates and/or diastereoisomers thereof:

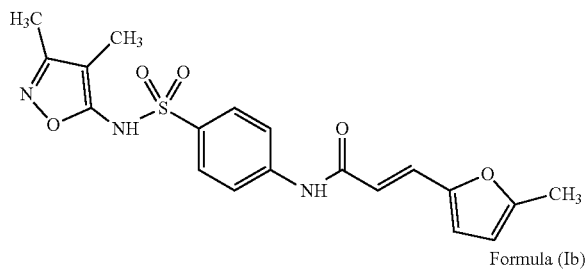

Formula (Ia)

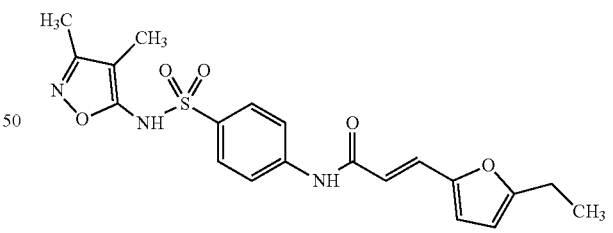

Formula (Ib)

8. The method according to claim 1, said compound being effective as an insulin sensitizer upon administration to the patient in need thereof.

9. The method according to claim 1, said compound being formulated in a pharmaceutical composition that is administered to the patient in need thereof.

10. A pharmaceutical composition, comprising at least one inhibitor compound selected from the group consisting of compounds belonging to the family of sulfonamide isoxazoles of Formula (I), and salts, solvates, and/or diastereoisomers thereof:

Formula (I)

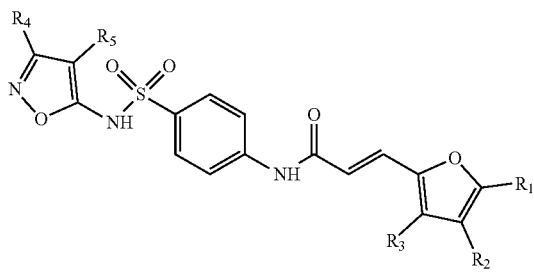

wherein:

the group $R_1$ represents a linear, cyclic or branched-chain alkyl group containing up to 5 carbon atoms, and the groups $R_2$, $R_3$, $R_4$, and $R_5$ are identical or different and represent a hydrogen atom or a linear, cyclic or branched-chain alkyl group containing up to 5 carbon atoms;

and at least one other active ingredient selected from: sulfonylureas, biguanides, thiazolidinediones, GLP1 analogues dipeptidyl peptidase-4 inhibitors alpha-glucosidase inhibitors, glinides, fibrates, and SGLT2 inhibitors.

11. The method according to claim 1, wherein said pathology associated with insulin resistance is selected from: metabolic syndrome, obesity, polycystic ovary syndrome, pre-gestational diabetes, type 2 diabetes, hyperglycemia, lipodystrophy, diabetic nephropathy, and cardiovascular complications, including high blood pressure, diabetic microangiopathy, or diabetic macroangiopathy.

12. The method according to claim 10, wherein said compound is administered at a dose between 50 mg and 250 mg per day.

13. A method for synthesizing a compound according to Formula (I) or its diastereoisomers:

Formula (I)

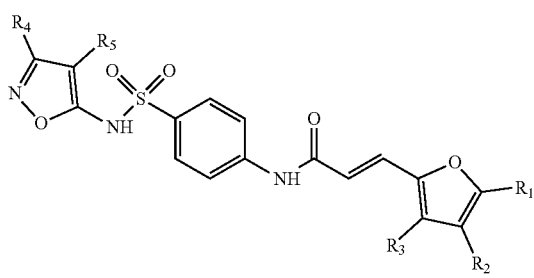

wherein:

the group $R_1$ in Formula (I) represents a linear, cyclic or branched-chain alkyl group containing up to 5 carbon atoms, and the groups $R_2$, $R_3$, $R_4$, and $R_5$ in Formula (I) are identical or different and represent a hydrogen atom or a linear, cyclic or branched-chain alkyl group containing up to 5 carbon atoms;

the method comprising a step of condensing a sulfonamide of Formula (V):

Formula (V)

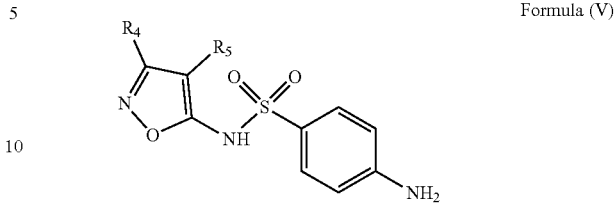

wherein:

the groups $R_4$ and $R_5$ are identical or different and represent a hydrogen atom or a linear, cyclic or branched-chain alkyl group containing up to 5 carbon atoms;

with an acrylic acid derivative of Formula (IV):

Formula (IV)

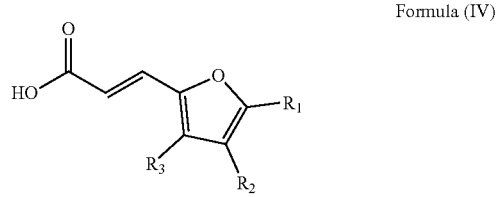

wherein:

the group $R_1$ represents a linear, cyclic or branched-chain alkyl group containing up to 5 carbon atoms, and the groups $R_2$ and $R_3$ are identical or different and represent a hydrogen atom or a linear, cyclic or branched-chain alkyl group containing up to 5 carbon atoms.

14. The method according to claim 13 wherein said condensation step is carried out in the presence of a peptide coupling reagent.

15. The method according to claim 13, wherein said condensation step is carried out in the presence of DIPEA (N-Ethyl-N-(propan-2-yl)propan-2-amine) and a peptide coupling reagent selected from HATU (1-[Bis(dimethylamino)methylene]-1H-1,2,3-triazolo[4,5-b]pyridinium,3-oxide hexafluorophosphate) and Ghosez's reagent (1-Chloro-N,N,2-trimethylpropenylamine).

16. The method according to claim 12, said dose being between 100 mg and 200 mg per day.

17. The method according to claim 10, said pharmaceutical composition further comprising at least one other active ingredient selected from: sulfonylureas, biguanides, thiazolidinediones, GLP1 analogues, dipeptidyl peptidase-4 inhibitors alpha-glucosidase inhibitors, glinides, fibrates, and SGLT2 inhibitors.

18. The method according to claim 17, wherein said at least one other active ingredient is selected from metformin, exenatide, liraglutide, sitagliptin, vildagliptin, saxagliptin, linagliptin, gemigliptin, alogliptin, and canaglifozin.

19. The pharmaceutical composition according to claim 10, wherein said at least one other active ingredient is selected from metformin, exenatide, liraglutide, sitagliptin, vildagliptin, saxagliptin, linagliptin, gemigliptin, alogliptin, and canaglifozin.

* * * * *